United States Patent
Sun et al.

(10) Patent No.: US 9,187,447 B2
(45) Date of Patent: *Nov. 17, 2015

(54) S-NITROSOGLUTATHIONE REDUCTASE INHIBITORS

(71) Applicant: N30 Pharmaceuticals, Inc., Boulder, CO (US)

(72) Inventors: Xicheng Sun, Broomfield, CO (US); Jian Qiu, Longmont, CO (US)

(73) Assignee: Nivalis Therapeutics, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/291,709

(22) Filed: May 30, 2014

(65) Prior Publication Data

US 2014/0275185 A1   Sep. 18, 2014

Related U.S. Application Data

(63) Continuation of application No. 13/521,833, filed as application No. PCT/US2011/024353 on Feb. 10, 2011, now Pat. No. 8,759,548.

(60) Provisional application No. 61/303,952, filed on Feb. 12, 2010.

(51) Int. Cl.
| | |
|---|---|
| C07D 311/76 | (2006.01) |
| A61K 31/35 | (2006.01) |
| C07D 311/22 | (2006.01) |
| C07D 311/58 | (2006.01) |
| C07D 335/06 | (2006.01) |
| C07D 405/10 | (2006.01) |
| C07D 409/04 | (2006.01) |
| C07D 413/10 | (2006.01) |
| C07D 417/10 | (2006.01) |
| C07D 311/36 | (2006.01) |
| C07D 407/08 | (2006.01) |
| C07D 409/10 | (2006.01) |

(52) U.S. Cl.
CPC ............ *C07D 311/22* (2013.01); *C07D 311/36* (2013.01); *C07D 311/58* (2013.01); *C07D 335/06* (2013.01); *C07D 405/10* (2013.01); *C07D 407/08* (2013.01); *C07D 409/04* (2013.01); *C07D 409/10* (2013.01); *C07D 413/10* (2013.01); *C07D 417/10* (2013.01)

(58) Field of Classification Search
USPC ........................................................ 549/403
See application file for complete search history.

(56) References Cited

U.S. PATENT DOCUMENTS

| | | | |
|---|---|---|---|
| 4,814,346 A | 3/1989 | Albert et al. | |
| 5,919,813 A | 7/1999 | de Juan, Jr. | |
| 8,481,590 B2 | 7/2013 | Sun et al. | |
| 8,669,381 B2 | 3/2014 | Sun et al. | |
| 8,759,548 B2 | 6/2014 | Sun et al. | |
| 2002/0128205 A1 | 9/2002 | Stamler et al. | |
| 2003/0181510 A1 | 9/2003 | Baker et al. | |
| 2004/0220180 A1 | 11/2004 | Glick | |
| 2005/0014697 A1 | 1/2005 | Stamler et al. | |
| 2005/0080024 A1 | 4/2005 | Tucker et al. | |
| 2005/0187166 A1 | 8/2005 | Stamler et al. | |
| 2005/0245603 A1 | 11/2005 | Druzgala et al. | |
| 2006/0247305 A1 | 11/2006 | Wang et al. | |
| 2006/0287388 A1 | 12/2006 | Druzgala et al. | |
| 2009/0029987 A1 | 1/2009 | Wong et al. | |
| 2010/0286174 A1 | 11/2010 | Stamler et al. | |
| 2012/0289555 A1 | 11/2012 | Sun et al. | |
| 2012/0295966 A1 | 11/2012 | Sun et al. | |
| 2014/0163092 A1 | 6/2014 | Sun et al. | |

FOREIGN PATENT DOCUMENTS

| | | |
|---|---|---|
| CN | 1475488 | 2/2004 |
| CN | 101365446 A | 2/2009 |
| WO | WO 97/31007 | 8/1997 |
| WO | WO 97/32872 | 9/1997 |
| WO | WO 00/10993 | 3/2000 |
| WO | WO 01/80855 | 11/2001 |
| WO | WO 02/055072 | 7/2002 |
| WO | WO 2004/002470 | 1/2004 |
| WO | WO 2004/037193 | 5/2004 |
| WO | WO 2006/099193 | 9/2006 |
| WO | WO 2007/016525 A2 | 2/2007 |
| WO | WO 2008/032105 | 3/2008 |
| WO | WO 2008/052256 | 5/2008 |
| WO | WO 2009/026657 | 3/2009 |
| WO | WO 2009/076665 | 6/2009 |
| WO | WO 2010/107476 | 9/2010 |
| WO | WO 2011/099978 | 8/2011 |
| WO | WO 2011/100433 | 8/2011 |

OTHER PUBLICATIONS de Belder et al. (May 1994) "Effects of S-nitroso-glutathione in the human forearm circulation; evidence for selective inhibition of platelet activation", *Cardiovasc Res.*, 28(5):691-694.

de Jesus-Berrios et al. (Nov. 2003) "Enzymes that Counteract Nitrosative Stress Promot Fungal Virulence", *Curr. Biol.*, 13:1963-1968.

Ding et al. (2005) "Efficient Synthesis of Isolflavone Analogues via a Suzuki Coupling Reaction" *Tetrahedron Letters* 46:3707-3709.

EP Search Report issued in EP 10845917.3 on Jun. 14, 2013.

EP Search Report issued in EP 11742796.3 on May 8, 2013.

Foster et al. (Apr. 2003) "S-nitrosylation in health and disease", *Trends in Molecular Medicine*, 9(4):160-168.

(Continued)

*Primary Examiner* — Nyeemah A Grazier

(74) *Attorney, Agent, or Firm* — Swanson & Bratschun, L.L.C.

(57) ABSTRACT

The present invention is directed to inhibitors of S-nitrosoglutathione reductase (GSNOR), pharmaceutical compositions comprising such GSNOR inhibitors, and methods of making and using the same.

2 Claims, No Drawings

(56) References Cited

OTHER PUBLICATIONS

Galietta et al. (Jun. 8, 2001) "Novel CFTR Chloride Channel Activators Identified by Screening of Combinatorial Librariers Based on Flavone and Benzoquinolizinium Lead Compounds" *J. Biol. Chem.* 276 (23):19723-19728.

Gaston et al. (Dec. 1993) "Endogenous nitrogen oxides and bronchodilator S-nitrosolthiols in human airways", *Proc. Natl. Acad. Sci. USA*, 90:10957-10961.

International Preliminary Report on Patentability mailed on Aug. 23, 2012 in PCT/US2010/024035.

International Preliminary Report on Patentability mailed on Aug. 23, 2012 in PCT/US2011/024353.

International Search Report and Written Opinion mailed Apr. 14, 2011 in PCT/US2011/024353.

International Search Report and Written Opinion mailed Apr. 2, 2010 in PCT/US2010/024035.

Jensen et al. (1998) "S-Nitrosoglutathione is a substrate for rat alcohol dehydrognease class III isoenzyme", *Biochem J.*, 331:659-668.

Kaposzta et al. (2002) "S-Nitrosoglutathione Reduces Asymptomatic Embolization After Carotid Angioplasty", *Circulation*, 106(24):3057-3062.

Lipton et al. (Sep. 2001) "S-Nitrosothiols signal the ventilatory response to hypoxia", *Nature*, 413:171-174.

Liu et al. (Feb. 2004) "Essential Roles of S-Nitrosothiols in Vascular Homeostatsis and Endotoxic Shock", *Cell*, 116(4):617-628.

Liu et al. (Mar. 2001) "A metabolic enzyme for S-nitrosothiol conserved from bacterial to humans", *Nature*, 410:490-494.

Martin et al., (2009) "7-Hydroxy-benzopyran-4-one Derivatives: A Novel Pharmacophone of Peroxisome Proliferator-Activated Receptor α- and γ-(PPARα and γ) Dual Agonists" *J. Med. Chem.*,52:6835-6850.

Patani et al. (1996) Che. Rev. 96:3147-3176, "Bioisosterism: A Rational Approach in Drug Design".

Que et al. (Jun. 2005) "Protection from Experimental Asthma by an Endogenous Bronchodilator", *Science*, 308(5728):1618-1621.

Sanghani et al. (2000) "Kinetic Mechanism of Human Glutathioone-Dependent Formaldehyde Dehydrogenase", *Biochemistry*, 39:10720-10729.

Sanghani et al. (2002) "Human Glutathione-Dependent Formaldehyde Dehydrognease. Structures of Apo, Binary, and Inhibitory Ternary Complexes", *Biochemistry*,41:10778-10786.

Scifinder search results for 4-[7-hydroxy-4-oxo-2-(trifluoromethyl)-4-H-chromen-3 yl] benzoic acid with the catalogue listings, Dec. 2009.

Sepulveda-Boza et al. (2001) "The Preparations of New Isoflavones" *Synthetic Communications*, 31(12):1933-1940.

Staab et al. (2008) "Dual functions of alcohol dehydrogenase 3: implications with focus on formaldehyde dehydrogenase and S-nitroglutathione reductase activities" *Cell Mol. Life Sci*, 65:3950-3960.

Staab et al. (Jun. 15, 2009) "Medium-chain fatty acids and glutathione derivatives as inhibitors of S-nitrosoglutathione reduction mediated by alcohol dehydrogenase 3", Chemico-Biological Interactions 180(1):113-118.

Stamler et al. (Aug. 1992) "Nitric oxide circulates in mammalian plasma primarily as an S-nitrose adduct of serium albumin", *Proc. Natl. Acad. Sci. USA*, 89:7674-7677.

Uotila and Koivusalo (1989) Coenzymes and Cofactors vol. 3: Glutathione, part A., D. Dolphin, ed. pp. 517-551 (New York, John Wiley & Sons).

Zaman et al. (2001) "S-Nitrosoglutathione Increases Cystic Fibrosis Transmembrane Regulator Maturation", *Biochem Biophys Res Commun.*, 284:65-70.

Foster, et al. (2009), Trends in Molecular Medicine 15(9):391-404, "Protein S-nitrosylation in health and disease: a current perspective."

S-NITROSOGLUTATHIONE REDUCTASE INHIBITORS

RELATED APPLICATIONS

This application is a continuation of U.S. application Ser. No. 13/521,833, filed Jul. 12, 2012. U.S. application Ser. No. 13/521,833 is a 35 U.S.C. §371 national phase application of International Application Serial No. PCT/US2011/024353, filed Feb. 10, 2011 (WO 2011/100433). International Application Serial No. PCT/US2011/024353 claims the benefit of U.S. Provisional Application Ser. No. 61/303,952, filed Feb. 12, 2010. Each of these applications is incorporated herein by reference in their entirety.

FIELD OF THE INVENTION

The present invention is directed to novel compounds, pharmaceutical compositions comprising such compounds, and methods of making and using the same. These compounds are useful as inhibitors of S-nitrosoglutathione reductase (GSNOR).

BACKGROUND

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, and neurotransmission, and plays a role in host defense. Although NO is highly reactive and has a lifetime of a few seconds, it can both diffuse freely across membranes and bind to many molecular targets. These attributes make NO an ideal signaling molecule capable of controlling biological events between adjacent cells and within cells.

NO is a free radical gas, which makes it reactive and unstable, thus NO is short lived in vivo, having a half life of 3-5 seconds under physiologic conditions. In the presence of oxygen, NO can combine with thiols to generate a biologically important class of stable NO adducts called S-nitrosothiols (SNO's). This stable pool of NO has been postulated to act as a source of bioactive NO and as such appears to be critically important in health and disease, given the centrality of NO in cellular homeostasis (Stamler et al., *Proc. Natl. Acad. Sci. USA,* 89:7674-7677 (1992)). Protein SNO's play broad roles in the function of cardiovascular, respiratory, metabolic, gastrointestinal, immune, and central nervous system (Foster et al., *Trends in Molecular Medicine,* 9 (4):160-168, (2003)). One of the most studied SNO's in biological systems is S-nitrosoglutathione (GSNO) (Gaston et al., *Proc. Natl. Acad. Sci. USA* 90:10957-10961 (1993)), an emerging key regulator in NO signaling since it is an efficient trans-nitrosating agent and appears to maintain an equilibrium with other S-nitrosated proteins (Liu et al., *Nature,* 410:490-494 (2001)) within cells. Given this pivotal position in the NO-SNO continuum, GSNO provides a therapeutically promising target to consider when NO modulation is pharmacologically warranted.

In light of this understanding of GSNO as a key regulator of NO homeostasis and cellular SNO levels, studies have focused on examining endogenous production of GSNO and SNO proteins, which occurs downstream from the production of the NO radical by the nitric oxide synthetase (NOS) enzymes. More recently there has been an increasing understanding of enzymatic catabolism of GSNO which has an important role in governing available concentrations of GSNO and consequently available NO and SNO's.

Central to this understanding of GSNO catabolism, researchers have recently identified a highly conserved S-nitrosoglutathione reductase (GSNOR) (Jensen et al., *Biochem J.,* 331:659-668 (1998); Liu et al., (2001)). GSNOR is also known as glutathione-dependent formaldehyde dehydrogenase (GSH-FDH), alcohol dehydrogenase 3 (ADH-3) (Uotila and Koivusalo, *Coenzymes and Cofactors.,* D. Dolphin, ed. pp. 517-551 (New York, John Wiley & Sons, 1989)), and alcohol dehydrogenase 5 (ADH-5). Importantly GSNOR shows greater activity toward GSNO than other substrates (Jensen et al., 1998; Liu et al., 2001) and appears to mediate important protein and peptide denitrosating activity in bacteria, plants, and animals. GSNOR appears to be the major GSNO-metabolizing enzyme in eukaryotes (Liu et al., 2001). Thus, GSNO can accumulate in biological compartments where GSNOR activity is low or absent (e.g., airway lining fluid) (Gaston et al., 1993).

Yeast deficient in GSNOR accumulates S-nitrosylated proteins which are not substrates of the enzyme, which is strongly suggestive that GSNO exists in equilibrium with SNO-proteins (Liu et al., 2001). Precise enzymatic control over ambient levels of GSNO and thus SNO-proteins raises the possibility that GSNO/GSNOR may play roles across a host of physiological and pathological functions including protection against nitrosative stress wherein NO is produced in excess of physiologic needs. Indeed, GSNO specifically has been implicated in physiologic processes ranging from the drive to breathe (Lipton et al., *Nature,* 413:171-174 (2001)) to regulation of the cystic fibrosis transmembrane regulator (Zaman et al., *Biochem Biophys Res Commun,* 284: 65-70 (2001)), to regulation of vascular tone, thrombosis, and platelet function (de Belder et al., *Cardiovasc Res.;* 28(5): 691-4 (1994)); (Z. Kaposzta, et al., *Circulation;* 106(24): 3057-3062, (2002)) as well as host defense (de Jesus-Berrios et al., *Curr. Biol.,* 13:1963-1968 (2003)). Other studies have found that GSNOR protects yeast cells against nitrosative stress both in vitro (Liu et al., 2001) and in vivo (de Jesus-Berrios et al., (2003)).

Collectively, data suggest GSNO as a primary physiological ligand for the enzyme S-nitrosoglutathione reductase (GSNOR), which catabolizes GSNO and consequently reduces available SNO's and NO in biological systems (Liu et al., (2001)), (Liu et al., *Cell,* 116(4), 617-628 (2004)), and (Que et al., *Science,* 308 (5728):1618-1621 (2005)). As such, this enzyme plays a central role in regulating local and systemic bioactive NO. Since perturbations in NO bioavailability has been linked to the pathogenesis of numerous disease states, including hypertension, atherosclerosis, thrombosis, asthma, gastrointestinal disorders, inflammation, and cancer, agents that regulate GSNOR activity are candidate therapeutic agents for treating diseases associated with NO imbalance.

Nitric oxide (NO), S-nitrosoglutathione (GSNO), and S-nitrosoglutathione reductase (GSNOR) regulate normal lung physiology and contribute to lung pathophysiology. Under normal conditions, NO and GSNO maintain normal lung physiology and function via their anti-inflammatory and bronchodilatory actions. Lowered levels of these mediators in pulmonary diseases such as asthma, chronic obstructive pulmonary disease (COPD) may occur via up-regulation of GSNOR enzyme activity. These lowered levels of NO and GSNO, and thus lowered anti-inflammatory capabilities, are key events that contribute to pulmonary diseases and which can potentially be reversed via GSNOR inhibition.

Inflammatory bowel diseases (IBD's), including Crohn's and ulcerative colitis, are chronic inflammatory disorders of the gastrointestinal (GI) tract, in which NO, GSNO, and GSNOR can exert influences. Under normal conditions, NO and GSNO function to maintain normal intestinal physiology via anti-inflammatory actions and maintenance of the intestinal epithelial cell barrier. In IBD, reduced levels of GSNO and NO are evident and likely occur via up-regulation of GSNOR activity. The lowered levels of these mediators contribute to the pathophysiology of IBD via disruption of the epithelial barrier via dysregulation of proteins involved in maintaining epithelial tight junctions. This epithelial barrier dysfunction, with the ensuing entry of micro-organisms from the lumen, and the overall lowered anti-inflammatory capabilities in the presence of lowered NO and GSNO, are key events in IBD progression that can be potentially influenced by targeting GSNOR.

Currently, there is a great need in the art for diagnostics, prophylaxis, ameliorations, and treatments for medical conditions relating to increased NO synthesis and/or increased NO bioactivity. In addition, there is a significant need for novel compounds, compositions, and methods for preventing, ameliorating, or reversing other NO-associated disorders. The present invention satisfies these needs.

SUMMARY

The present invention provides novel compounds (Formula I). These compounds are useful as S-nitrosoglutathione reductase ("GSNOR") inhibitors. The invention encompasses pharmaceutically acceptable salts, prodrugs, metabolites, and stereoisomers of the described compounds. Also encompassed by the invention are pharmaceutical compositions comprising at least one compound of the invention and at least one pharmaceutically acceptable carrier.

The compositions of the present invention can be prepared in any suitable pharmaceutically acceptable dosage form.

The present invention provides a method for inhibiting GSNOR in a subject in need thereof. Such a method comprises administering a therapeutically effective amount of a pharmaceutical composition comprising at least one GSNOR inhibitor or a pharmaceutically acceptable salt, prodrug, metabolite, or stereoisomer thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a disorder ameliorated by NO donor therapy in a subject in need thereof. Such a method comprises administering a therapeutically effective amount of a pharmaceutical composition comprising at least one GSNOR inhibitor or a pharmaceutically acceptable salt thereof, a prodrug, metabolite, or stereoisomer thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a cell proliferative disorder in a subject in need thereof. Such a method comprises administering a therapeutically effective amount of a pharmaceutical composition comprising at least one GSNOR inhibitor or a pharmaceutically acceptable salt, prodrug, metabolite, or stereoisomer thereof, in combination with at least one pharmaceutically acceptable carrier. The GSNOR inhibitor can be a novel compound according to the invention, or it can be a known compound which previously was not known to be an inhibitor of GSNOR.

The methods of the invention encompass administration with one or more secondary active agents. Such administration can be sequential or in a combination composition.

Although methods and materials similar or equivalent to those described herein can be used in the practice or testing of the present invention, suitable methods and materials are described below. All publicly available publications, patent applications, patents, and other references mentioned herein are incorporated by reference in their entirety. In the case of conflict, the present specification, including definitions, will control.

Both the foregoing summary and the following detailed description are exemplary and explanatory and are intended to provide further details of the compositions and methods as claimed. Other objects, advantages, and novel features will be readily apparent to those skilled in the art from the following detailed description.

DETAILED DESCRIPTION

A. Overview of the Invention

Until recently, S-nitrosoglutathione reductase (GSNOR) was known to oxidize the formaldehyde glutathione adduct, S-hydroxymethylglutathione. GSNOR has since been identified in a variety of bacteria, yeasts, plants, and animals and is well conserved. The proteins from *E. coli, S. cerevisiae* and mouse macrophages share over 60% amino acid sequence identity. GSNOR activity (i.e., decomposition of GSNO when NADH is present as a required cofactor) has been detected in *E. coli*, in mouse macrophages, in mouse endothelial cells, in mouse smooth muscle cells, in yeasts, and in human HeLa, epithelial, and monocyte cells. Human GSNOR nucleotide and amino acid sequence information can be obtained from the National Center for Biotechnology Information (NCBI) databases under Accession Nos. M29872, NM_000671. Mouse GSNOR nucleotide and amino acid sequence information can be obtained from NCBI databases under Accession Nos. NM_007410. In the nucleotide sequence, the start site and stop site are underlined. CDS designates coding sequence. SNP designates single nucleotide polymorphism. Other related GSNOR nucleotide and amino acid sequences, including those of other species, can be found in U.S. Patent Application 2005/0014697.

In accord with the present invention, GSNOR has been shown to function in vivo and in vitro to metabolize S-nitrosoglutathione (GSNO) and protein S-nitrosothiols (SNOs) to modulate NO bioactivity, by controlling the intracellular levels of low mass NO donor compounds and preventing protein nitrosylation from reaching toxic levels.

Based on this, it follows that inhibition of this enzyme potentiates bioactivity in diseases in which NO donor therapy is indicated, inhibits the proliferation of pathologically proliferating cells, and increases NO bioactivity in diseases where this is beneficial.

The present invention provides pharmaceutical agents that are potent inhibitors of GSNOR. In particular, provided are analogs having the structures depicted below (Formula I), or a pharmaceutically acceptable salt, stereoisomer, prodrug, or metabolite thereof.

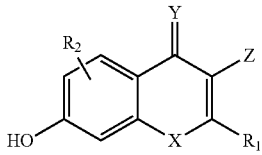
(I)

wherein
X is selected from the group consisting of O and S;
Y is selected from the group consisting of O and S;
Z is selected from the group consisting of $Z_1$, $Z_2$, $Z_3$, and $Z_4$, wherein
$Z_1$ is

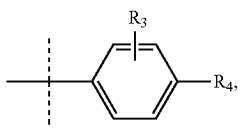

$Z_2$ is

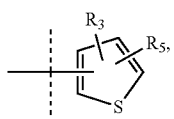

$Z_3$ is

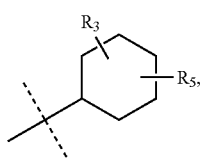

and
$Z_4$ is

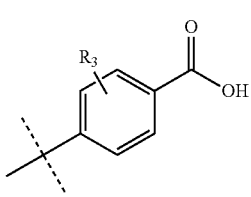

provided that Z is only $Z_4$ when at least one of X or Y is S;
$R_1$ is selected from the group consisting of hydrogen, $(C_1$-$C_6)$ alkyl, $(C_3$-$C_7)$cycloalkyl, $(C_1$-$C_6)$haloalkyl, unsubstituted aryl$(C_1$-$C_4)$alkyl, substituted aryl$(C_1$-$C_6)$alkyl, $(C_1$-$C_6)$ heteroalkyl, substituted or unsubstituted aryl, and substituted or unsubstituted heteroaryl;
$R_2$ is selected from the group consisting of hydrogen, halogen, cyano, and $(C_1$-$C_6)$ alkoxy;
$R_3$ is selected from the group consisting of hydrogen, halogen, $(C_1$-$C_6)$ alkyl, $(C_1$-$C_6)$ haloalkyl, $(C_1$-$C_6)$ alkoxy, cyano, and N,N-dimethylamino;
$R_4$ is selected from the group consisting of tetrazole, oxadiazolone, thiadiazolone, methylsulfonylcarbamoyl, and N-hydroxycarbamoyl; and $R_5$ is selected from the group consisting of carboxy, tetrazole, oxadiazolone, thiadiazolone, methylsulfonylcarbamoyl, and N-hydroxycarbamoyl.

Further, in any of the compositions described herein, one or more compounds or subgenus of compounds can be specifically excluded.

As used in this context, the term "analog" refers to a compound having similar chemical structure and function as compounds of Formula I that retains the central ring system.

Some analogs of the invention can also exist in various stereoisomeric forms, including configurational, geometric, and conformational isomers, as well as existing in various tautomeric forms, particularly those that differ in the point of attachment of a hydrogen atom. As used herein, the term "stereoisomer" or is intended to encompass such isomeric forms of a compound including tautomeric forms of the compound.

Illustrative compounds having asymmetric centers can exist in different enantiomeric and diastereomeric forms. A compound can exist in the form of an optical isomer or a diastereomer. Accordingly, the invention encompasses compounds in the forms of their optical isomers, diastereomers and mixtures thereof, including racemic mixtures.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of the described compound.

B. S-Nitrosoglutathione Reductase Inhibitors

1. Inventive Compounds

In one of its aspects the present invention provides a compound having a structure shown in Formula I, or a pharmaceutically acceptable salt, stereoisomer, prodrug, or metabolite thereof:

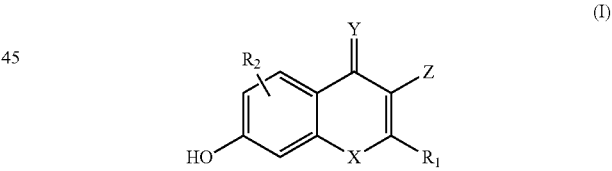
(I)

wherein
X is selected from the group consisting of O and S;
Y is selected from the group consisting of O and S;
Z is selected from the group consisting of $Z_1$, $Z_2$, $Z_3$, and $Z_4$, wherein
$Z_1$ is

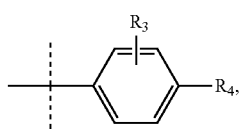

$Z_2$ is

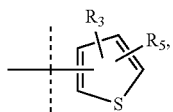

$Z_3$ is

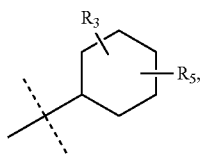

and
$Z_4$ is

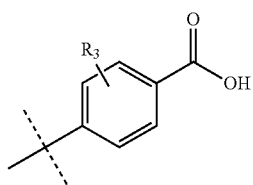

provided that Z is only $Z_4$ when at least one of X or Y is S;

$R_1$ is selected from the group consisting of hydrogen, ($C_1$-$C_6$) alkyl, ($C_3$-$C_7$)cycloalkyl, ($C_1$-$C_6$)haloalkyl, unsubstituted aryl($C_1$-$C_4$)alkyl, substituted aryl($C_1$-$C_6$)alkyl, ($C_1$-$C_6$) heteroalkyl, substituted or unsubstituted aryl, and substituted or unsubstituted heteroaryl;

$R_2$ is selected from the group consisting of hydrogen, halogen, cyano, and ($C_1$-$C_6$) alkoxy;

$R_3$ is selected from the group consisting of hydrogen, halogen, ($C_1$-$C_6$) alkyl, ($C_1$-$C_6$) haloalkyl, ($C_1$-$C_6$) alkoxy, cyano, and N,N-dimethylamino;

$R_4$ is selected from the group consisting of tetrazole, oxadiazolone, thiadiazolone, methylsulfonylcarbamoyl, and N-hydroxycarbamoyl; and $R_5$ is selected from the group consisting of carboxy, tetrazole, oxadiazolone, thiadiazolone, methylsulfonylcarbamoyl, and N-hydroxycarbamoyl.

In a further aspect of the invention, $R_4$ is selected from the group consisting of tetrazole, 1,2,4-oxadiazol-5(4H)-one-3-yl, 1,2,4-thiadiazol-5(4H)-one-3-yl, 1,3,4-oxadiazol-2(3H)-one-5-yl, 1,3,4-thiadiazol-2(3H)-one-5-yl, 1,2,4-thiadiazol-3(2H)-one-5-yl, 1,2,4-oxadiazol-3(2H)-one-5-yl, methylsulfonylcarbamoyl, and N-hydroxycarbamoyl; and $R_5$ is selected from the group consisting of carboxy, tetrazole, 1,2,4-oxadiazol-5(4H)-one-3-yl, 1,2,4-thiadiazol-5(4H)-one-3-yl, 1,3,4-oxadiazol-2(3H)-one-5-yl, 1,3,4-thiadiazol-2(3H)-one-5-yl, 1,2,4-thiadiazol-3(2H)-one-5-yl, 1,2,4-oxadiazol-3(2H)-one-5-yl, methylsulfonylcarbamoyl, and N-hydroxycarbamoyl.

In a further aspect of the invention, $R_1$ is selected from the group consisting of hydrogen, $CF_3$, $CF_2H$, $CF_2CH_3$, $CF_2CH_2CH_3$, methyl, isopropyl, isobutyl, cyclopentyl, $CH_2OCH_3$, $SCH_3$, benzyl, 4-carboxy benzyl, thiophen-2-yl, and thiophen-3-yl;

$R_2$ is selected from the group consisting of hydrogen, fluoro, chloro, methoxy, and cyano; and $R_3$ is selected from the group consisting of hydrogen, fluoro, chloro, methyl, $CF_3$, methoxy, cyano, and N,N-dimethylamino.

In a further aspect of the invention, $R_1$ is selected from the group consisting of hydrogen, $CF_3$, $CF_2H$, methyl, and 4-carboxybenzyl;

$R_2$ is selected from the group consisting of hydrogen and fluoro;

$R_3$ is selected from the group consisting of hydrogen, fluoro, chloro, and methyl;

$R_4$ is selected from the group consisting of tetrazole, 1,2,4-oxadiazol-5(4H)-one-3-yl, 1,2,4-thiadiazol-5(4H)-one-3-yl, 1,3,4-oxadiazol-2(3H)-one-5-yl, methylsulfonylcarbamoyl, and N-hydroxycarbamoyl; and $R_5$ is selected from the group consisting of carboxy, tetrazole, 1,2,4-oxadiazol-5(4H)-one-3-yl, 1,2,4-thiadiazol-5(4H)-one-3-yl, 1,3,4-oxadiazol-2(3H)-one-5-yl, methylsulfonylcarbamoyl, and N-hydroxycarbamoyl.

In a further aspect of the invention, $R_4$ is selected from the group consisting of tetrazole, 1,2,4-oxadiazol-5(4H)-one-3-yl, 1,2,4-thiadiazol-5(4H)-one-3-yl, methylsulfonylcarbamoyl, and N-hydroxycarbamoyl; and $R_5$ is selected from the group consisting of carboxy, tetrazole, 1,2,4-oxadiazol-5(4H)-one-3-yl, 1,2,4-thiadiazol-5(4H)-one-3-yl, methylsulfonylcarbamoyl, and N-hydroxycarbamoyl.

In a further aspect of the invention, X is selected from the group consisting of O and S. In another aspect of the invention, X is O. In yet another aspect of the invention, X is S.

In a further aspect of the invention, Y is selected from the group consisting of O and S. In another aspect of the invention Y is O. In yet another aspect of the invention, Y is S.

In a further aspect of the invention, suitable compounds of Formula I include, but are not limited to:

3-(4-(1H-tetrazol-5-yl)phenyl)-7-hydroxy-2-(trifluoromethyl)-4H-chromen-4-one;

5-(7-hydroxy-4-oxo-2-(trifluoromethyl)-4H-chromen-3-yl)thiophene-2-carboxylic acid;

(trans)-4-(7-hydroxy-4-oxo-2-(trifluoromethyl)-4H-chromen-3-yl)cyclohexanecarboxylic acid;

(cis)-4-(7-hydroxy-4-oxo-2-(trifluoromethyl)-4H-chromen-3-yl)cyclohexanecarboxylic acid;

3-(4-(1H-tetrazol-5-yl)phenyl)-2-(difluoromethyl)-7-hydroxy-4H-chromen-4-one;

3-(4-(1H-tetrazol-5-yl)phenyl)-7-hydroxy-2-methyl-4H-chromen-4-one;

4-(2-(4-carboxybenzyl)-7-hydroxy-4-oxo-4H-thiochromen-3-yl)benzoic acid;

4-(7-hydroxy-2-methyl-4-oxo-4H-thiochromen-3-yl)benzoic acid;

3-(4-(7-hydroxy-4-oxo-2-(trifluoromethyl)-4H-chromen-3-yl)phenyl)-1,2,4-oxadiazol-5(4H)-one;

4-(7-hydroxy-4-oxo-2-(trifluoromethyl)-4H-chromen-3-yl)-N-(methylsulfonyl)benzamide;

3-(4-(7-hydroxy-4-oxo-2-(trifluoromethyl)-4H-chromen-3-yl)phenyl)-1,2,4-thiadiazol-5(4H)-one;

3-(4-(1H-tetrazol-5-yl)phenyl)-7-hydroxy-2-methyl-4H-thiochromen-4-one;

5-(7-hydroxy-4-oxo-2-(trifluoromethyl)-4H-chromen-3-yl)thiophene-3-carboxylic acid;

3-((trans)-4-(1H-tetrazol-5-yl)cyclohexyl)-7-hydroxy-2-(trifluoromethyl)-4H-chromen-4-one;

N-hydroxy-4-(7-hydroxy-4-oxo-2-(trifluoromethyl)-4H-chromen-3-yl)benzamide;

3-(2-chloro-4-(1H-tetrazol-5-yl)phenyl)-7-hydroxy-2-(trifluoromethyl)-4H-chromen-4-one;

3-(3-chloro-4-(7-hydroxy-4-oxo-2-(trifluoromethyl)-4H-chromen-3-yl)phenyl)-1,2,4-oxadiazol-5(4H)-one;

3-(3-fluoro-4-(7-hydroxy-4-oxo-2-(trifluoromethyl)-4H-chromen-3-yl)phenyl)-1,2,4-oxadiazol-5(4H)-one;

3-(3-chloro-4-(1H-tetrazol-5-yl)phenyl)-7-hydroxy-2-(trifluoromethyl)-4H-chromen-4-one; and 3-(4-(1H-tetrazol-5-yl)phenyl)-7-hydroxy-4H-chromen-4-one; and 5-(4-(7-hydroxy-4-oxo-2-(trifluoromethyl)-4H-chromen-3-yl)phenyl)-1,3,4-oxadiazol-2(3H)-one.

In a further embodiment, the compound 3-fluoro-4-(7-hydroxy-4-oxo-2-(trifluoromethyl)-4H-chromen-3-yl)benzoic acid is a compound of the invention.

In a further embodiment, the compound 4-(7-hydroxy-4-oxo-2-(trifluoromethyl)-4H-chromen-3-yl)-3-methylbenzoic acid is a compound of the invention.

In a further embodiment, the compound 4-(8-fluoro-7-hydroxy-4-oxo-2-(trifluoromethyl)-4H-chromen-3-yl)benzoic acid is a compound of the invention.

Examples of $Z_1$ wherein $R_4$ is tetrazole, 1,2,4-oxadiazol-5(4H)-one-3-yl, 1,2,4-thiadiazol-5(4H)-one-3-yl, 1,3,4-oxadiazol-2(3H)-one-5-yl, 1,3,4-thiadiazol-2(3H)-one-5-yl, 1,2,4-thiadiazol-3(2H)-one-5-yl, 1,2,4-oxadiazol-3(2H)-one-5-yl, methylsulfonylcarbamoyl, and N-hydroxycarbamoyl include, respectively

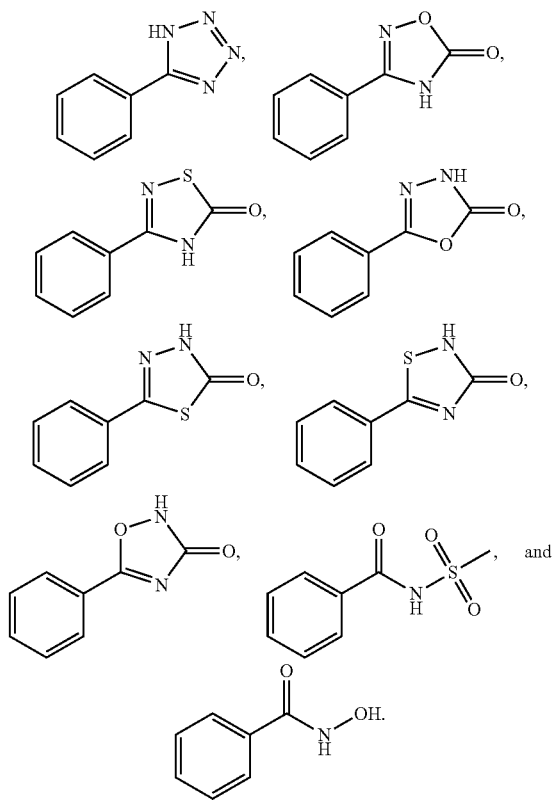

Examples of $Z_3$ wherein $R_5$ is carboxy, tetrazole, 1,2,4-oxadiazol-5(4H)-one-3-yl, 1,2,4-thiadiazol-5(4H)-one-3-yl, 1,3,4-oxadiazol-2(3H)-one-5-yl, 1,3,4-thiadiazol-2(3H)-one-5-yl, 1,2,4-thiadiazol-3(2H)-one-5-yl, 1,2,4-oxadiazol-3(2H)-one-5-yl, methylsulfonylcarbamoyl, and N-hydroxycarbamoyl include, respectively

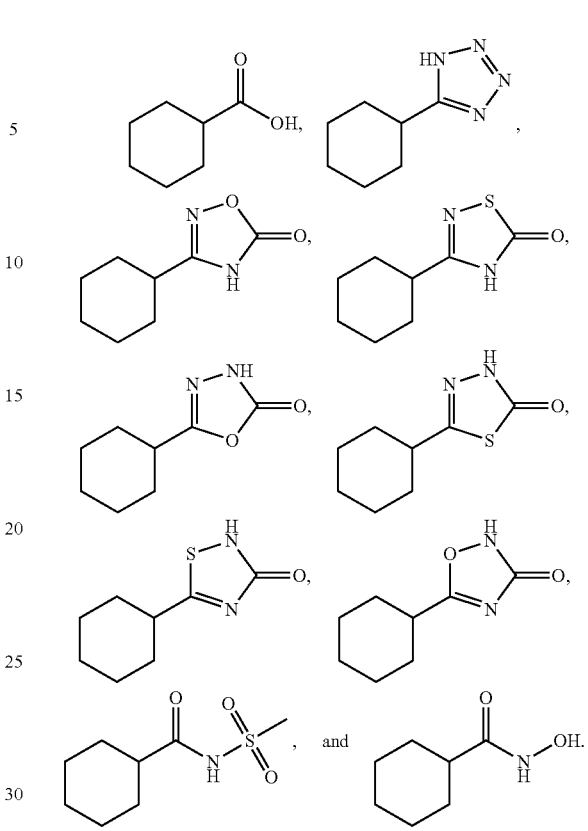

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood that isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

2. Representative Compounds

The examples provided below list representative novel analogs of the invention. The synthetic methods that can be used to prepare each compound are detailed in Examples 1-24, with reference to intermediates described in Example 25. Supporting mass spectrometry data and/or proton NMR data for each compound is also included in Examples 1-22. GSNOR inhibitor activity was determined by the assay described in Example 26 and $IC_{50}$ values were obtained for Examples 1-22. GSNOR inhibitor compounds in Examples 1-22 had an $IC_{50}$ of about <1 μM. GSNOR inhibitor compounds in Examples 1-3,5-6, 8-9, 11-12, 14, 16-22 had an $IC_{50}$ of about less than 0.1 μM.

C. Definitions

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "acyl" includes compounds and moieties that contain the acetyl radical ($CH_3CO$—) or a carbonyl group to which a straight or branched chain lower alkyl residue is attached.

The term "alkyl" as used herein refers to a straight or branched chain, saturated hydrocarbon having the indicated number of carbon atoms. For example, ($C_1$-$C_6$) alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein.

The term "alkenyl" as used herein refers to a straight or branched chain unsaturated hydrocarbon having the indicated number of carbon atoms and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein.

The term "alkynyl" as used herein refers to a straight or branched chain unsaturated hydrocarbon having the indicated number of carbon atoms and at least one triple bond. Examples of a ($C_2$-$C_8$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne, and 4-octyne. An alkynyl group can be unsubstituted or optionally substituted with one or more substituents as described herein.

The term "alkoxy" as used herein refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl" as used herein, refers to an alkyl group (typically one to six carbon atoms) wherein one or more of the $C_1$-$C_6$ alkyl group's hydrogen atoms is replaced with an amine of formula —$N(R^c)_2$, wherein each occurrence of $R^c$ is independently —H or ($C_1$-$C_6$) alkyl. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl, and the like.

The term "aryl" as used herein refers to a 5- to 14-membered monocyclic, bicyclic, or tricyclic aromatic ring system. Examples of an aryl group include phenyl and naphthyl. An aryl group can be unsubstituted or optionally substituted with one or more substituents as described herein below. Examples of aryl groups include phenyl or aryl heterocycles such as, pyrrole, furan, thiophene, thiazole, isothiazole, imidazole, triazole, tetrazole, pyrazole, oxazole, isoxazole, pyridine, pyrazine, pyridazine, and pyrimidine, and the like.

As used herein, the term "bioactivity" indicates an effect on one or more cellular or extracellular process (e.g., via binding, signaling, etc.) which can impact physiological or pathophysiological processes.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxy" or "carboxyl" means a —COOH group or carboxylic acid.

The term "$C_m$-$C_n$" means "m" number of carbon atoms to "n" number of carbon atoms. For example, the term "$C_1$-$C_6$" means one to six carbon atoms ($C_1$, $C_2$, $C_3$, $C_4$, $C_5$, or $C_6$). The term "$C_2$-$C_6$" includes two to six carbon atoms ($C_2$, $C_3$, $C_4$, $C_5$, or $C_6$). The term "$C_3$-$C_6$" includes three to six carbon atoms ($C_3$, $C_4$, $C_5$, or $C_6$).

The term "cycloalkyl" as used herein refers to a 3- to 14-membered saturated or unsaturated non-aromatic monocyclic, bicyclic, or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, tetrahydroheptalene, (1s,3s)-bicyclo[1.1.0]butane, bicyclo[1.1.1]pentane, bicyclo[2.1.1]hexane, Bicyclo[2.2.1]heptane, bicyclo[2.2.2]octane, bicyclo[3.1.1]heptane, bicyclo[3.2.1]octane, bicyclo[3.3.1]nonane, bicyclo[3.3.2]decane, bicyclo[3.3.]undecane, bicyclo[4.2.2]decane, and bicyclo[4.3.1]decane. A cycloalkyl group can be unsubstituted or optionally substituted with one or more substituents as described herein below.

The term "halogen" includes fluorine, bromine, chlorine, iodine, etc.

The term "haloalkyl," as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl," by itself or in combination with another term, means, unless otherwise stated, a stable straight or branched chain alkyl, or combinations thereof, consisting of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N, and S can be placed at any position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, and —$CH_2$—CH=N—$OCH_3$. Up to two heteroatoms can be consecutive, for example, —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group can be an oxyalkyl group. For instance, ($C_2$-$C_5$) oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2OH$, —$OCH_2CH_2OCH_2CH_2OH$, —$OCH_2CH(OH)CH_2OH$, and the like.

As used herein, "arylalkyl" refers to an -alkyl-aryl group, wherein the arylalkyl group is covalently linked to the defined chemical structure via the alkyl group. An example of an arylalkyl group is a benzyl group (—$CH_2$—$C_6H_5$). An arylalkyl group can be optionally substituted, i.e., the aryl group and/or the alkyl group can be substituted as disclosed herein.

The term "heteroaryl" as used herein refers to an aromatic heterocycle ring of 5 to 14 members and having at least one heteroatom selected from nitrogen, oxygen, and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thienyl, benzothienyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen, and sulfur, and wherein the nitrogen and sulfur heteroatoms can be optionally oxidized, and the nitrogen heteroatom can be optionally quaternized, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom, where chemically acceptable. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thienyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "heterocycloalkyl," by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl," as used herein, refers to an alkyl group having the indicated number of carbon atoms wherein one or more of the hydrogen atoms in the alkyl group is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "hydroxy" or "hydroxyl" includes groups with an —OH or —$O^-$.

As used herein, N-oxide, or amine oxide, refers to a compound derived from a tertiary amine by the attachment of one oxygen atom to the nitrogen atom, $R_3N^+$—$O^-$. By extension the term includes the analogous derivatives of primary and secondary amines.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein, "protein" is used synonymously with "peptide," "polypeptide," or "peptide fragment". A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" is meant to refer to an increase or decrease in the levels of a peptide or a polypeptide, or to increase or decrease the stability or activity of a peptide or a polypeptide. The term "inhibit" is meant to refer to a decrease in the levels of a peptide or a polypeptide or to a decrease in the stability or activity of a peptide or a polypeptide. In preferred embodiments, the peptide which is modulated or inhibited is S-nitrosoglutathione (GSNO) or protein S-nitrosothiols (SNOs).

As used here, the terms "nitric oxide" and "NO" encompass uncharged nitric oxide and charged nitric oxide species, particularly including nitrosonium ion ($NO^+$) and nitroxyl ion ($NO^-$). The reactive form of nitric oxide can be provided by gaseous nitric oxide. Compounds having the structure X—NO$_y$, wherein X is a nitric oxide releasing, delivering, or transferring moiety, including any and all such compounds which provide nitric oxide to its intended site of action in a form active for their intended purpose, and Y is 1 or 2.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a compound of the invention is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, and K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

Substituents for the groups referred to as alkyl, heteroalkyl, alkylene, alkenyl, alkynyl, cycloalkyl, heterocycloalkyl, cycloalkenyl, and heterocycloalkenyl can be selected from a variety of groups including —OR$^{d}$, =O, =NR$^{d}$, =N—OR$^{d}$, —NR$^{d}$R$^{d''}$, —SR$^{d}$, -halo, —SiR$^{d}$R$^{d''}$R$^{d'''}$, —OC(O)R$^{d}$, —C(O)R$^{d}$, —CO$_2$R$^{d}$, —CONR$^{d}$R$^{d''}$, —OC(O)NR$^{d}$R$^{d''}$, —NR$^{d''}$C(O)R$^{d}$, —NR$^{d''}$C(O)NR$^{d}$R$^{d''}$, —NR$^{d'''}$SO$_2$NR$^{d}$R$^{d''}$, —NR$^{d''}$CO$_2$R$^{d}$, —NHC(NH$_2$)=NH, —NR$^{a''}$C(NH$_2$)=NH, —NHC(NH$_2$)=NR$^{d}$, —SO$_2$R$^{d}$, —SO$_2$R$^{d}$, —SO$_2$NR$^{d}$R$^{d''}$, —NR$^{d'''}$SO$_2$R$^{d}$, —CN, and —NO$_2$, in a number ranging from zero to three, with those groups having zero, one or two substituents being exemplary.

R$^{d}$, R$^{d''}$, and R$^{d'''}$ each independently refer to hydrogen, unsubstituted (C$_1$-C$_8$)alkyl, unsubstituted hetero(C$_1$-C$_8$) alkyl, unsubstituted aryl, and aryl substituted with one to three substituents selected from -halo, unsubstituted alkyl, unsubstituted alkoxy, unsubstituted thioalkoxy, and unsubstituted aryl (C$_1$-C$_4$)alkyl. When R$^{d}$ and R$^{d''}$ are attached to the same nitrogen atom, they can be combined with the nitrogen atom to form a 5-, 6-, or 7-membered ring. For example, —NR$^{d}$R$^{d''}$ can represent 1-pyrrolidinyl or 4-morpholinyl.

Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted.

Exemplary substituents for the alkyl and heteroalkyl radicals include, but are not limited to —OR$^{d}$, =O, =NR$^{d}$, =N—OR$^{d}$, —NR$^{d}$R$^{d''}$, —SR$^{d}$, -halo, —SiR$^{d}$R$^{d''}$R$^{d'''}$, —OC(O)R$^{d}$, —C(O)R$^{d}$, —CO$_2$R$^{d}$, —CONR$^{d}$R$^{d''}$, —OC(O)NR$^{d}$R$^{d''}$, —NR$^{d''}$C(O)R$^{d}$, —NR$^{d''}$C(O)NR$^{d}$R$^{d''}$, —NR$^{d'''}$SO$_2$NR$^{d}$R$^{d''}$, —NR$^{d''}$CO$_2$R$^{d}$, —NHC(NH$_2$)=NH, —NR$^{a''}$C(NH$_2$)=NH, —NHC(NH$_2$)=NR$^{d}$, —S(O)R$^{d}$, —SO$_2$R$^{d}$, —SO$_2$NR$^{d}$R$^{d''}$, —NR$^{d''}$SO$_2$R$^{d}$, —CN, and —NO$_2$, where R$^{d}$, R$^{d''}$, and R$^{d'''}$ are as defined above. Typical substituents can be selected from: —OR$^{d''}$, =O, —NR$^{d}$R$^{d''}$, -halo, —OC(O)R$^{d}$, —CO$_2$R$^{d}$, —C(O)NR$^{d}$R$^{d''}$, —OC(O)NR$^{d}$R$^{d''}$, —NR$^{d''}$C(O)R$^{d}$, —NR$^{d''}$CO$_2$R$^{d}$, —NR$^{d'''}$SO$_2$NR$^{d}$R$^{d''}$, —SO$_2$R$^{d}$, —SO$_2$NR$^{d}$R$^{d''}$, —NR$^{d''}$SO$_2$R$^{d}$, —CN, and —NO$_2$.

Similarly, substituents for the aryl and heteroaryl groups are varied and selected from: -halo, —OR$^{e'}$, —OC(O)R$^{e'}$, —NR$^{e'}$R$^{e''}$, —SR$^{e'}$, —R$^{e'}$, —CN, —NO$_2$, —CO$_2$R$^{e'}$, —C(O)NR$^{e'}$R$^{e''}$, —C(O)R$^{e'}$, —OC(O)NR$^{e'}$R$^{e''}$, —NR$^{e''}$C(O)R$^{e'}$, —NR$^{e''}$CO$_2$R$^{e'}$, —NR$^{e'''}$C(O)NR$^{e'}$R$^{e''}$, —NR$^{e'''}$SO$_2$NR$^{e'}$R$^{e''}$, —NHC(NH$_2$)=NH, —NR$^{e'}$C(NH$_2$)=NH, —NH—C(NH$_2$)=NR$^{e'}$, —S(O)R$^{e'}$, —SO$_2$R$^{e'}$, —SO$_2$NR$^{e'}$R$^{e''}$, —NR$^{e''}$SO$_2$R$^{e'}$, —N$_3$, —CH(Ph)$_2$, perfluoroalkoxy, and perfluoro(C$_1$-C$_4$)alkyl, in a number ranging from zero to the total number of open valences on the aromatic ring system.

R$^{e'}$, R$^{e''}$ and R$^{e'''}$ are independently selected from hydrogen, unsubstituted (C$_1$-C$_8$) alkyl, unsubstituted hetero(C$_1$-C$_8$) alkyl, unsubstituted aryl, unsubstituted heteroaryl, unsubstituted aryl(C$_1$-C$_4$) alkyl, and unsubstituted aryloxy (C$_1$-C$_4$) alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein may optionally be replaced with a substituent of the formula -T-C(O)—(CH$_2$)$_q$-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -J-(CH$_2$)$_r$-K-, wherein J and K are independently —CH$_2$—, —O—, —NH—, —S—, —S(O)—, —S(O)$_2$—, —S(O)$_2$NR$^{f'}$—, or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^{f'}$—, —S—, —S(O)—, —S(O)$_2$—, or —S(O)$_2$NR$^{a'}$—. The substituent R$^{f'}$ in —NR$^{f'}$— and —S(O)$_2$NR$^{f'}$— is selected from hydrogen or unsubstituted (C$_1$-C$_6$) alkyl.

"Stable compound" and "stable structure" are meant to indicate a compound that is sufficiently robust to survive isolation to a useful degree of purity from a reaction mixture, and formulation into an efficacious therapeutic agent.

As used herein the term "therapeutically effective amount" generally means the amount necessary to ameliorate at least one symptom of a disorder to be prevented, reduced, or treated as described herein. The phrase "therapeutically effective amount" as it relates to the GSNOR inhibitors of the present invention shall mean the GSNOR inhibitor dosage that provides the specific pharmacological response for which the GSNOR inhibitor is administered in a significant number of subjects in need of such treatment. It is emphasized that a therapeutically effective amount of a GSNOR inhibitor that is administered to a particular subject in a particular instance will not always be effective in treating the conditions/diseases described herein, even though such dosage is deemed to be a therapeutically effective amount by those of skill in the art.

The term "biological sample" includes, but is not limited to, samples of blood (e.g., serum, plasma, or whole blood), urine, saliva, sweat, breast milk, vaginal secretions, semen, hair follicles, skin, teeth, bones, nails, or other secretions, body fluids, tissues, or cells. In accordance with the invention, the levels of the GSNOR in the biological sample can be determined by the methods described in U.S. Patent Application Publication No. 2005/0014697.

D. Pharmaceutical Compositions

The invention encompasses pharmaceutical compositions comprising at least one compound of the invention described herein and at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

The pharmaceutical compositions of the invention can comprise novel compounds described herein, the pharmaceutical compositions can comprise known compounds which previously were not known to have GSNOR inhibitor activity, or a combination thereof.

The compounds of the invention can be utilized in any pharmaceutically acceptable dosage form, including, but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the compounds of the invention described herein can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets, and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory infections, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol, or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates, or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes, or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.), or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the compounds of the invention are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions according to the invention comprising at least one compound of the invention can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

E. Kits Comprising the Compositions of the Invention

The present invention also encompasses kits comprising the compositions of the invention. Such kits can comprise, for example, (1) at least one compound of the invention; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial, or similar apparatus for holding and/or mixing the kit components; and (3) delivery apparatus, such as an inhaler, nebulizer, syringe, etc.

F. Methods of Preparing Compounds of the Invention

The compounds of the invention can readily be synthesized using known synthetic methodologies or via a modification of known synthetic methodologies. As would be readily recognized by a skilled artisan, the methodologies described below allow the synthesis of analogs having a variety of substituents. Exemplary synthetic methods are described in the Examples section below.

If needed, further purification and separation of enantiomers and diastereomers can be achieved by routine procedures known in the art. Thus, for example, the separation of enantiomers of a compound can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

Synthetic steps that require a base are carried out using any convenient organic or inorganic base. Typically, the base is not nucleophilic. Thus, in one embodiment, the base is selected from carbonates, phosphates, hydroxides, alkoxides, salts of disilazanes, and tertiary amines.

The process of the invention, when performed as described herein, can be substantially complete after several minutes to after several hours depending upon the nature and quantity of reactants and reaction temperature. The determination of when the reaction is substantially complete can be conveniently evaluated by ordinary techniques known in the art such as, for example, HPLC, LCMS, TLC, and $^1$H NMR.

G. Methods of Treatment

The invention encompasses methods of preventing or treating (e.g., alleviating one or more symptoms of) medical conditions through use of one or more of the disclosed compounds. The methods comprise administering a therapeutically effective amount of a compound of the invention to a patient in need. The compositions of the invention can also be used for prophylactic therapy.

The compound of the invention used in the methods of treatment according to the invention can be: (1) a novel compound described herein, or a pharmaceutically acceptable salt thereof, a prodrug thereof, a metabolite thereof, or a stereoisomer thereof; (2) a compound which was known prior to the present invention, but wherein it was not known that the compound is a GSNOR inhibitor, or a pharmaceutically acceptable salt thereof, a prodrug thereof, a metabolite thereof, or a stereoisomer thereof; or (3) a compound which was known prior to the present invention, and wherein it was known that the compound is a GSNOR inhibitor, but wherein it was not known that the compound is useful for the methods of treatment described herein, or a pharmaceutically acceptable salt thereof, a prodrug thereof, a metabolite thereof, or a stereoisomer thereof.

The patient can be any animal, domestic, livestock, or wild, including, but not limited to cats, dogs, horses, pigs, and cattle, and preferably human patients. As used herein, the terms patient and subject may be used interchangeably.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition, or disorder. More specifically, "treating" includes reversing, attenuating, alleviating, minimizing, suppressing, or halting at least one deleterious symptom or effect of a disease (disorder) state, disease progression, disease causative agent (e.g., bacteria or viruses), or other abnormal condition. Treatment is continued as long as symptoms and/or pathology ameliorate.

In general, the dosage, i.e., the therapeutically effective amount, ranges from 1 µg/kg to 10 g/kg and often ranges from 10 µg/kg to 1 g/kg or 10 µg/kg to 100 mg/kg body weight of the subject being treated, per day.

H. GSNOR Uses

In subjects with deleteriously high levels of GSNOR or GSNOR activity, modulation may be achieved, for example, by administering one or more of the disclosed compounds that disrupt or down-regulates GSNOR function, or decreases GSNOR levels. These compounds may be administered with other GSNOR inhibitor agents, such as anti-GSNOR antibodies or antibody fragments, GSNOR antisense, iRNA, or small molecules, or other inhibitors, alone or in combination with other agents as described in detail herein.

The present invention provides a method of treating a subject afflicted with a disorder ameliorated by NO donor therapy. Such a method comprises administering to a subject a therapeutically effective amount of a GSNOR inhibitor.

The disorders can include pulmonary disorders associated with hypoxemia and/or smooth muscle constriction in the lungs and airways and/or lung infection and/or lung inflammation and/or lung injury (e.g., pulmonary hypertension, ARDS, asthma, pneumonia, pulmonary fibrosis/interstitial lung diseases, cystic fibrosis, COPD); cardiovascular disease and heart disease (e.g., hypertension, ischemic coronary syndromes, atherosclerosis, heart failure, glaucoma); diseases characterized by angiogenesis (e.g., coronary artery disease); disorders where there is risk of thrombosis occurring; disorders where there is risk of restenosis occurring; inflammatory diseases (e.g., AIDS related dementia, inflammatory bowel disease (IBD), Crohn's disease, colitis, and psoriasis); functional bowel disorders (e.g., irritable bowel syndrome (IBS)); diseases where there is risk of apoptosis occurring (e.g., heart failure, atherosclerosis, degenerative neurologic disorders, arthritis, and liver injury (ischemic or alcoholic)); impotence; sleep apnea; diabetic wound healing; cutaneous infections; treatment of psoriasis; obesity caused by eating in response to craving for food; stroke; reperfusion injury (e.g., traumatic muscle injury in heart or lung or crush injury); and disorders where preconditioning of heart or brain for NO protection against subsequent ischemic events is beneficial, central nervous system (CNS) disorders (e.g., anxiety, depression, psychosis, and schizophrenia); and infections caused by bacteria (e.g., tuberculosis, *C. difficile* infections, among others).

In one embodiment, the compounds of the present invention or a pharmaceutically acceptable salt thereof, or a prodrug, stereoisomer, or metabolite thereof, can be administered in combination with an NO donor. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso, and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy (N-nitrosamine), and perfluorocarbons that have been saturated with NO or a hydrophobic NO donor.

The combination of a GSNOR inhibitor with R(+) enantiomer of amlodipine, a known NO releaser (Zhang at al., *J. Cardiovasc. Pharm.* 39: 208-214 (2002)) is also an embodiment of the present invention.

The present invention also provides a method of treating a subject afflicted with pathologically proliferating cells where the method comprises administering to said subject a therapeutically effective amount of an inhibitor of GSNOR. The inhibitors of GSNOR are the compounds as defined above, or a pharmaceutically acceptable salt thereof, or a prodrug or metabolite or stereoisomer thereof, in combination with a pharmaceutically acceptable carrier. Treatment is continued as long as symptoms and/or pathology ameliorate.

In another embodiment, the pathologically proliferating cells can be pathologically proliferating microbes. The microbes involved can be those where GSNOR is expressed to protect the microbe from nitrosative stress or where a host cell infected with the microbe expresses the enzyme, thereby protecting the microbe from nitrosative stress. The term "pathologically proliferating microbes" is used herein to mean pathologic microorganisms including, but not limited to, pathologic bacteria, pathologic viruses, pathologic *Chlamydia*, pathologic protozoa, pathologic *Rickettsia*, pathologic fungi, and pathologic mycoplasmata. More detail on the applicable microbes is set forth at columns 11 and 12 of U.S. Pat. No. 6,057,367. The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium* leper (leprosy), or *Salmonella typhi* (typhoid fever).

In another embodiment, the pathologically proliferating cells can be pathologic helminths. The term "pathologic helminths" is used herein to refer to pathologic nematodes, pathologic trematodes and pathologic cestodes. More detail on the applicable helminths is set forth at column 12 of U.S. Pat. No. 6,057,367.

In another embodiment, the pathologically proliferating cells can be pathologically proliferating mammalian cells. The term "pathologically proliferating mammalian cells" as used herein means cells of the mammal that grow in size or number in said mammal so as to cause a deleterious effect in the mammal or its organs. The term includes, for example, the pathologically proliferating or enlarging cells causing restenosis, the pathologically proliferating or enlarging cells causing benign prostatic hypertrophy, the pathologically proliferating cells causing myocardial hypertrophy, and proliferating cells at inflammatory sites such as synovial cells in arthritis or cells associated with a cell proliferation disorder.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration. The cell proliferative disorder can be a precancerous condition or cancer. The cancer can be primary cancer or metastatic cancer, or both.

As used herein, the term "cancer" includes solid tumors, such as lung, breast, colon, ovarian, pancreas, prostate, adenocarcinoma, squamous carcinoma, sarcoma, malignant glioma, leiomyosarcoma, hepatoma, head and neck cancer, malignant melanoma, non-melanoma skin cancers, as well as hematologic tumors and/or malignancies, such as leukemia, childhood leukemia and lymphomas, multiple myeloma, Hodgkin's disease, lymphomas of lymphocytic and cutaneous origin, acute and chronic leukemia such as acute lymphoblastic, acute myelocytic, or chronic myelocytic leukemia, plasma cell neoplasm, lymphoid neoplasm, and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses, and the like. In one embodiment, proliferative diseases include dysplasias and disorders of the like.

In one embodiment, treating cancer comprises a reduction in tumor size, decrease in tumor number, a delay of tumor growth, decrease in metastaic lesions in other tissues or organs distant from the primary tumor site, an improvement in the survival of patients, or an improvement in the quality of patient life, or at least two of the above.

In another embodiment, treating a cell proliferative disorder comprises a reduction in the rate of cellular proliferation, reduction in the proportion of proliferating cells, a decrease in size of an area or zone of cellular proliferation, or a decrease in the number or proportion of cells having an abnormal appearance or morphology, or at least two of the above.

In yet another embodiment, the compounds of the present invention or a pharmaceutically acceptable salt thereof, a prodrug thereof, a stereoisomer thereof, or a metabolite thereof can be administered in combination with a second chemotherapeutic agent. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In one embodiment, the compounds of the present invention or a pharmaceutically acceptable salt thereof, a prodrug thereof, a stereoisomer thereof, or a metabolite thereof can be administered in combination with an agent that imposes nitrosative or oxidative stress. Agents for selectively imposing nitrosative stress to inhibit proliferation of pathologically proliferating cells in combination therapy with GSNOR inhibitors herein and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with GSNOR inhibitors herein include, for example, L-buthionine-5-sulfoximine (BSO), glutathione reductase inhibitors (e.g., BCNU), inhibitors or uncouplers of mitochondrial respiration, and drugs that increase reactive oxygen species (ROS), e.g., adriamycin, in standard dosages with standard routes of administration.

GSNOR inhibitors may also be co-administered with a phosphodiesterase inhibitor (e.g., rolipram, cilomilast, roflumilast, Viagra® (sildenifil citrate), Clalis® (tadalafil), Levitra® (vardenifil), etc.), a β-agonist, a steroid, or a leukotriene antagonist (LTD-4). Those skilled in the art can readily determine the appropriate therapeutically effective amount depending on the disorder to be ameliorated.

GSNOR inhibitors may be used as a means to improve β-adrenergic signaling. In particular, inhibitors of GSNOR alone or in combination with β-agonists could be used to treat or protect against heart failure, or other vascular disorders such as hypertension and asthma. GSNOR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels).

The therapeutically effective amount for the treatment of a subject afflicted with a disorder ameliorated by NO donor therapy is the GSNOR inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective amount is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by troponin or CPK.

The therapeutically effective amount for the treatment of a subject afflicted with pathologically proliferating cells means a GSNOR inhibiting amount in vivo which is an antiproliferative effective amount. Such antiproliferative effective amount as used herein means an amount causing reduction in rate of proliferation of at least about 20%, at least about 10%, at least about 5%, or at least about 1%.

I. Uses in an Apparatus

The compounds of the present invention or a pharmaceutically acceptable salt thereof, or a prodrug or metabolite or stereoisomer thereof, can be applied to various apparatus in circumstances when the presence of such compounds would be beneficial. Such apparatus can be any device or container, for example, implantable devices in which a compound of the invention can be used to coat a surgical mesh or cardiovascular stent prior to implantation in a patient. The compounds of the invention can also be applied to various apparatus for in vitro assay purposes or for culturing cells.

The compounds of the present invention or a pharmaceutically acceptable salt thereof, or a prodrug, a stereoisomer, or a metabolite thereof can also be used as an agent for the development, isolation or purification of binding partners to compounds of the invention, such as antibodies, natural ligands, and the like. Those skilled in the art can readily determine related uses for the compounds of the present invention.

EXAMPLES

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Examples 1-24 list representative novel analogs of the invention useful as GSNOR inhibitors. Synthetic methods that can be used to prepare each compound are described in Examples 1-24. Supporting mass spectrometry data and/or proton NMR data is also included in Examples 1-22. Synthetic details for corresponding Intermediates are detailed in Example 25.

Example 1

3-(4-(1H-tetrazol-5-yl)phenyl)-7-hydroxy-2-(trifluoromethyl)-4H-chromen-4-one

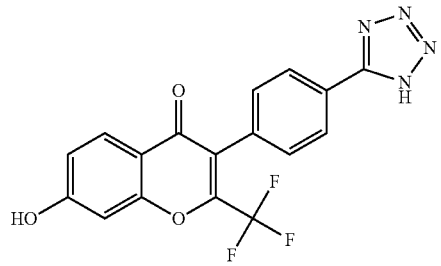 [SMILES: O=c1c(-c2ccc(-c3nnn[nH]3)cc2)c(C(F)(F)F)oc2cc(O)ccc12]

Synthesis: Step 1: Synthesis of 4-(7-hydroxy-4-oxo-2-(trifluoromethyl)-4H-chromen-3-yl)benzonitrile. To a solution of 4-(2-(2,4-dihydroxyphenyl)-2-oxoethyl)benzamide (Intermediate A) (300 mg, 1.08 mmol) and triethylamine (TEA) (0.6 ml, 4.32 mmol) in DCM (6 ml) was added TFAA (1.2 ml, 8.64 mmol) dropwise 0° C. The mixture was stirred at room temperature for 2 hours. The mixture was then washed with 1N HCl solution (5 ml), sat NaHCO$_3$ (5 ml) and brine (5 ml). The organic phase was dried over Na$_2$SO$_4$, concentrated and purified by prep-TLC (PE (petroleum ether): EtOAc=3:1) to afford product as yellow oil (66 mg, 19.5%). MS (ESI): m/z 332.1 [M+1]$^+$.

Step 2: Synthesis of 3-(4-(1H-tetrazol-5-yl)phenyl)-7-hydroxy-2-(trifluoromethyl)-4H-chromen-4-one. To a solution of 4-(7-hydroxy-4-oxo-2-(trifluoromethyl)-4H-chromen-3-yl)benzonitrile (50 mg, 0.15 mmol) in toluene (2 ml), was added TMSN$_3$ (296 mg, 2.72 mmol) and Bu$_2$SnO (10 mg, 0.045 mmol) at room temperature. The mixture was refluxed overnight. The volatiles were removed under reduced pressure. The residue was purified by prep-HPLC to afford desired product in Example 1 as a yellow powder (19.4 mg, 34.6%).

Data: $^1$H NMR (MeOH-d$_4$ 500 MHz TMS): 8.12 (d, J=8.5 Hz, 2H), 8.02 (d, J=8.5 Hz, 2H), 7.52 (d, J=8.5 Hz, 2H), 7.02 (dd, J=1.5 Hz, J=8.5 Hz, 1H), 6.94 (d, J=1.5 Hz, 1H); MS (ESI): m/z 375.0 [M+1]+.

Example 2

5-(7-hydroxy-4-oxo-2-(trifluoromethyl)-4H-chromen-3-yl)thiophene-2-carboxylic acid

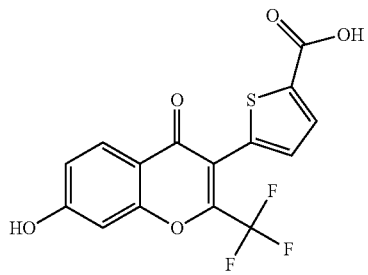 [SMILES: O=C(O)c1ccc(-c2c(C(F)(F)F)oc3cc(O)ccc3c2=O)s1]

Synthesis: Step 1: Synthesis of methyl 5-(7-hydroxy-4-oxo-2-(trifluoromethyl)-4H-chromen-3-yl)thiophene-2-carboxylate. Followed the procedure described in Step 1 of Example 1, starting with Intermediate B. MS (ESI): m/z 371.0 [M+1]$^+$.

Step 2: Synthesis of 5-(7-hydroxy-4-oxo-2-(trifluoromethyl)-4H-chromen-3-yl)thiophene-2-carboxylic acid. To a solution of methyl 5-(7-hydroxy-4-oxo-2-(trifluoromethyl)-4H-chromen-3-yl)thiophene-2-carboxylate (295 mg, 0.80 mmol) in dioxane (1.5 ml) was added concentrated HCl (1.5 ml). The reaction mixture was stirred at 70° C. for 24 hours, cooled to room temperature and centrifuged. The precipitate was rinsed with water (2 ml×2), DCM (2 ml×2) and dried in vacuo to afford the desired product in Example 2 as a gray powder (216.1 mg, 76.3%).

Data: $^1$H NMR (MeOD-d$_4$ 500 MHz TMS): 8.04 (d, J=8.5 Hz, 1H), 7.78 (d, J=3.5 Hz, 1H), 7.13 (d, J=4.0 Hz, 1H), 7.04 (dd, J=2.0 Hz, J=8.5 Hz, 1H), 6.96 (d, J=2.0 Hz, 1H); MS (ESI): m/z 357.0 [M+1]$^+$.

Example 3

(trans)-4-(7-hydroxy-4-oxo-2-(trifluoromethyl)-4H-chromen-3-yl)cyclohexanecarboxylic acid

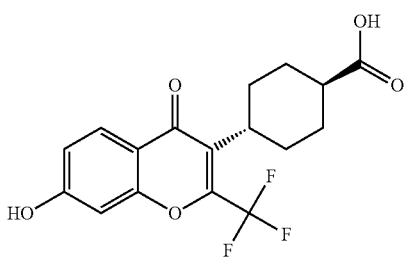 [SMILES: O=c1c2ccc(O)cc2oc(C(F)(F)F)c1[C@H]1CC[C@H](C(=O)O)CC1]

Synthesis: Step 1: Synthesis of ethyl 4-(7-hydroxy-4-oxo-2-(trifluoromethyl)-4H-chromen-3-yl)cyclohexanecarboxylate. Followed procedure described in Step 1 of Example 1, starting with Intermediate C where the crude product was used directly without workup or purification. MS (ESI): m/z 385.1[M+1]$^+$.

Step 2: To a solution of ethyl 4-(7-hydroxy-4-oxo-2-(trifluoromethyl)-4H-chromen-3-yl)cyclohexanecarboxylate (450 mg, 1.1 mmol) in dioxane (3 ml) was added conc. HCl (3 ml). The solution was stirred at 75° C. overnight. The mixture was concentrated in vacuo to give a yellow solid, which was purified by prep-HPLC to afford the pure trans isomer, the desired product in Example 3 (100 mg, 24%).

Data: $^1$H NMR (MeOH-d$_4$ 500 MHz TMS): δ 7.97 (d, J=9.0 Hz, 2H), 6.97 (dd, J=2.0, 8.5 Hz, 1H), 6.84 (d, J=2.5 Hz, 1H), 2.71 (t, J=12.0 Hz, 1H), 2.38-2.48 (m, 3H), 2.05-2.14 (m, 2H), 1.65-1.68 (m, 2H), 1.44-1.53 (m, 2H); MS (ESI): m/z 357.0[M+1]$^+$.

Example 4

(cis)-4-(7-hydroxy-4-oxo-2-(trifluoromethyl)-4H-chromen-3-yl)cyclohexanecarboxylic acid

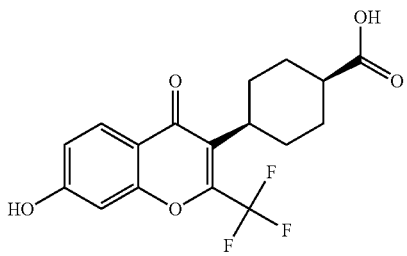 [SMILES: O=c1c2ccc(O)cc2oc(C(F)(F)F)c1[C@H]1CC[C@@H](C(=O)O)CC1]

Synthesis: See Example 3 for details. Prep-HPLC gave 64 mg, 15.3% of the pure cis isomer, the desired product in Example 4.

Data: $^1$H NMR (MeOH-d$_4$ 500 MHz TMS): δ 7.93 (d, J=9.0 Hz, 1H), 6.95 (dd, J=2.5, 9.0 Hz, 1H), 6.83 (d, J=2.0 Hz, 1H), 2.77-2.71 (m, 2H), 2.50-2.58 (m, 2H), 2.33 (s, 2H), 1.55-1.62 (m, 2H), 1.45-1.47 (m, 2H); MS (ESI): m/z 357.0 [M+1]$^+$.

Example 5

3-(4-(1H-tetrazol-5-yl)phenyl)-2-(difluoromethyl)-7-hydroxy-4H-chromen-4-one

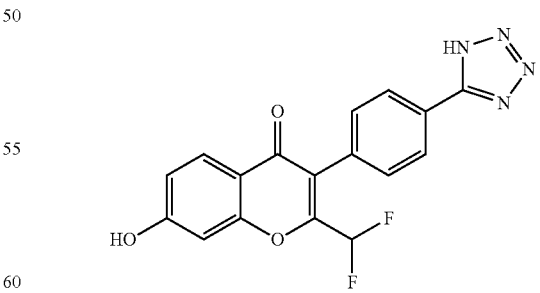

Synthesis: Followed the procedure described in Step 1 of Example 1, starting with Intermediate D and difluoroacetic anhydride.

Data: $^1$H NMR (MeOH-d$_4$ 500 MHz TMS): δ 8.18 (d, J=8.5 Hz, 2H), 8.07 (d, J=8.5 Hz, 1H), 7.58 (d, J=8.5 Hz, 2H), 7.03 (dd, J=2.5 Hz, J=9.0 Hz, 1H), 6.98 (d, J=2.0 Hz, 1H), 6.56 (t, J=2.0 Hz, 1H); MS (ESI): m/z 357.0 [M+1]+.

Example 6

3-(4-(1H-tetrazol-5-yl)phenyl)-7-hydroxy-2-methyl-4H-chromen-4-one

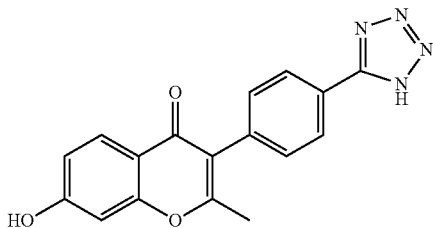 [SMILES: Cc1oc2cc(O)ccc2c(=O)c1-c1ccc(-c2nnn[nH]2)cc1]

Synthesis: Followed the procedure described in Step 1 of Example 1, starting with Intermediate D and acetic anhydride. The crude product was purified by prep-HPLC to give Example 6.

Data: $^1$H NMR (DMSO-d$_6$ 500 MHz TMS): δ 10.84 (s, 1H), 8.09 (d, J=8.5 Hz, 2H), 7.90 (d, J=9.0 Hz,1H), 7.53 (d, J=8.5 Hz, 2H), 6.93 (dd, J=2.5 Hz, J=8.5 Hz, 1H), 6.87 (d, J=2.5 Hz, 1H), 2.29 (s, 3H); MS (ESI): m/z 321.0 [M+1]+.

Example 7

4-(2-(4-carboxybenzyl)-7-hydroxy-4-oxo-4H-thiochromen-3-yl)benzoic acid

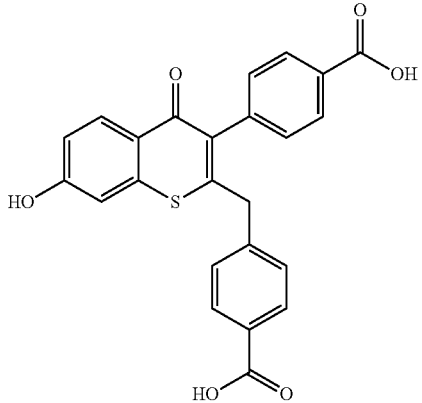 [SMILES: O=C(O)c1ccc(Cc2sc3cc(O)ccc3c(=O)c2-c2ccc(C(=O)O)cc2)cc1]

Synthesis: Step 1: Synthesis of methyl 4-(7-methoxy-2-(4-(methoxycarbonyl)benzyl)-4-oxo-4H-thiochromen-3-yl) benzoate. Aluminum trichloride (253 mg, 1.9 mmol) was added to Intermediate E (methyl 4-(2-(3-methoxyphenylthio)-2-oxoethyl)benzoate) (500 mg, 1.58 mmol) and the mixture was heated at 130° C. for 1 hour. After cooling to room temperature, the reaction mixture was dissolved in EtOAc (50 ml) and washed with 1 N icy HCl (25 ml×2), water (25 ml) and brine (25 ml), dried over Na$_2$SO$_4$, filtered and concentrated in vacuo. The residue was purified by Combi-Flash (40 g silica gel, fluent: PE:EtOAc=10:0 to 1:1 by gradient, 40 ml/min, 30 min, 1.2 L total solvent volume) to afford product as a yellow solid (160 mg, 21%). MS (ESI): m/z 475.1 [M+1]+.

Step 2: Synthesis of 4-(2-(4-carboxybenzyl)-7-hydroxy-4-oxo-4H-thiochromen-3-yl)benzoic acid (Example 7). To a solution of methyl 4-(7-methoxy-2-(4-(methoxycarbonyl)benzyl)-4-oxo-4H-thiochromen-3-yl)benzoate (105 mg, 0.23 mmol) in dry DCM (3 ml) was added BBr$_3$ (0.2 ml, 2.23 mmol) at 0° C. with stirring. The mixture was stirred at room temperature for 40 hours and poured into 1 N icy HCl solution (1 ml) with stirring. The volatiles were evaporated and the residue was purified by prep-TLC (PE:EtOAc=1:1) to afford the desired product in Example 7 as a pink solid (15 mg, 16%).

Data: $^1$H NMR (MeOH-d$_4$ 500 MHz TMS): δ 8.30 (d, J=9.0 Hz, 1H), 8.08 (d, J=8.0 Hz, 2H), 7.91 (d, J=8.0 Hz, 2H), 7.28 (d, J=8.0 Hz, 2H), 7.18 (d, J=8.0 Hz, 2H), 7.053 (d, J=7.5 Hz, 1H), 7.049 (s, 1H), 4.01 (s, 2H); MS (ESI): m/z 433.0 [M+1]+.

Example 8

4-(7-hydroxy-2-methyl-4-oxo-4H-thiochromen-3-yl)benzoic acid

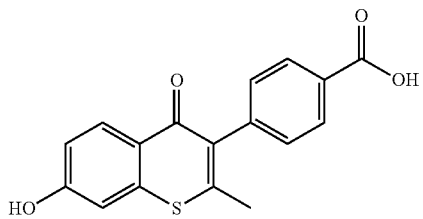 [SMILES: Cc1sc2cc(O)ccc2c(=O)c1-c1ccc(C(=O)O)cc1]

Synthesis: Step 1: Synthesis of methyl 4-(7-methoxy-2-methyl-4-oxo-4H-thiochromen-3-yl)benzoate: To a solution of Intermediate F (methyl 4-(2-(2-(acetylthio)-4-methoxyphenyl)-2-oxoethyl)benzoate) (600 mg, 1.674 mmol) in acetone (12 ml) was added K$_2$CO$_3$ (386 mg, 3.348 mmol) at room temperature. The mixture was stirred for 3 hours, filtered and concentrated. The residue was purified by Combi-Flash (40 g silica gel, start PE/EtOAc=10/0 to 3/1 gradient, 40 ml/min, 40 min, 1.6 L total solvent volume) to afford the product as a yellow solid (400 mg, 70%). MS (ESI): m/z 341.0 [M+1]+.

Step 2: Synthesis of 4-(7-hydroxy-2-methyl-4-oxo-4H-thiochromen-3-yl)benzoic acid (Example 8): To a solution of methyl 4-(7-methoxy-2-methyl-4-oxo-4H-thiochromen-3-yl)benzoate (200 mg, 0.588 mmol) in DCM (10 ml) was added BBr$_3$ (0.83 ml, 8.813 mmol) at room temperature and stirred for 20 hours. The mixture was poured into icy 1 N HCl (50 ml) with stirring and the precipitate was collected by filtration to obtain crude product, which was purified by prep-HPLC to afford the desired product in Example 8 as a yellow solid (57.3 mg, 31%).

Data: $^1$H NMR (DMSO-d$_6$ 500 MHz TMS): δ 13.00 (brs, 1H), 10.76 (brs, 1H), 8.16 (d, J=9.0 Hz, 1H), 7.98 (d, J=8.5

Hz, 2H), 7.32 (d, J=8.0 Hz, 2H), 7.03-7.08 (m, 2H), 2.17 (s, 3H); MS (ESI): m/z 313.0 [M+1]+.

Example 9

3-(4-(7-hydroxy-4-oxo-2-(trifluoromethyl)-4H-chromen-3-yl)phenyl)-1,2,4-oxadiazol-5(4H)-one

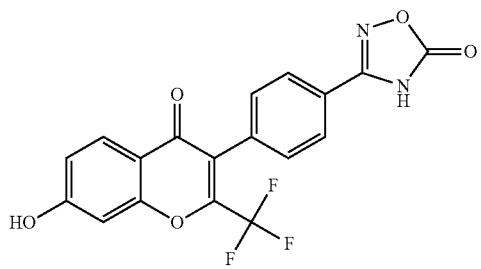 [SMILES: O=c1[nH]c(-c2ccc(-c3c(C(F)(F)F)oc4cc(O)ccc4c3=O)cc2)no1]

Synthesis: To a solution of 4-(7-hydroxy-4-oxo-2-(trifluoromethyl)-4H-chromen-3-yl)benzonitrile (see Example 1, step 1 for synthesis) (200 mg, 0.60 mmol) and hydroxylamine hydrochloride (218 mg, 3.13 mmol) in absolute ethanol (2 ml) was added dropwise triethylamine (0.7 ml). The resulting mixture was heated to reflux for 5 hours. The volatiles were evaporated and the residue was dissolved in anhydrous THF (2 ml). CDI (296 mg, 1.83 mmol) was added and the suspension was heated to reflux overnight. The volatiles were evaporated and the residue was purified by prep-TLC (pure EtOAc) and prep-HPLC to afford desired product in Example 9 (35 mg, 15%) as a white solid.

Data: $^1$H NMR (MeOH-$d_4$ 500 MHz TMS): δ 8.04 (d, J=9.0 Hz, 1H), 7.89 (d, J=8.5 Hz, 2H), 7.50 (d, J=8.5 Hz, 2H), 7.04 (dd, J=2.5 Hz, J=8.5 Hz, 1H), 6.87 (d, J=2.5 Hz, 1H); MS (ESI): m/z 391.0 [M+1]+.

Example 10

4-(7-hydroxy-4-oxo-2-(trifluoromethyl)-4H-chromen-3-yl)-N-(methylsulfonyl)benzamide

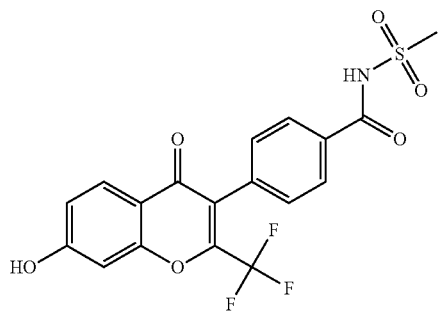 [SMILES: CS(=O)(=O)NC(=O)c1ccc(-c2c(C(F)(F)F)oc3cc(O)ccc3c2=O)cc1]

Synthesis: To a solution of 4-(7-hydroxy-4-oxo-2-(trifluoromethyl)-4H-chromen-3-yl)benzoic acid (synthesis is described in PCT/US2010/024035) (100 mg, 0.28 mmol) in THF (10 ml) was added CDI (139 mg, 0.86 mmol) at room temperature. The mixture was stirred for 2 hours. MeSO$_2$NH$_2$ (280 mg, 2.86 mmol) was added in one portion, followed by DBU (394 mg, 2.86 mmol). The mixture was stirred for 4 hours and partitioned between 1N HCl (30 ml) and ethyl acetate (100 ml). The organic phase was separated, washed with brine (50 ml), dried over Na$_2$SO$_4$ and concentrated to give the desired product contaminated with the acid starting material. The mixture was difficult to purify and the acid contaminant was converted into the methyl ester by treatment with SOCl$_2$ (91 mg, 0.77 mmol) in MeOH (4 ml) at 0° C. When the addition was complete, the mixture was stirred for 3 days. The volatiles were removed under reduced pressure and the residue was purified by prep-HPLC to afford the desired product in Example 10 as a white powder (25 mg, 20.5%).

Data: $^1$H NMR (MeOH-$d_4$ 500 MHz TMS): δ 8.04 (d, J=8.5 Hz, 1H), 8.00 (d, J=8.5 Hz, 2H), 7.46 (d, J=8.5 Hz, 2H), 7.04 (dd, J=2.0 Hz, J=9.0 Hz, 1H), 6.97 (d, J=2.0 Hz, 1H), 3.41 (s, 1H); MS (ESI): m/z 428.0 [M+1]+.

Example 11

3-(4-(7-hydroxy-4-oxo-2-(trifluoromethyl)-4H-chromen-3-yl)phenyl)-1,2,4-thiadiazol-5(4H)-one

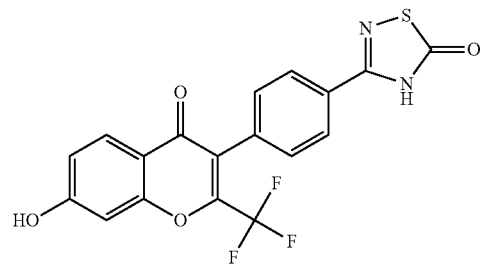 [SMILES: O=c1[nH]c(-c2ccc(-c3c(C(F)(F)F)oc4cc(O)ccc4c3=O)cc2)ns1]

Synthesis: To a solution of 4-(7-hydroxy-4-oxo-2-(trifluoromethyl)-4H-chromen-3-yl)benzonitrile (see Example 1, step 1 for synthesis) (250 mg, 0.76 mmol) and hydroxylamine hydrochloride (105 mg, 1.51 mmol) in absolute ethanol (2 ml) was added dropwise triethylamine (0.5 ml). The resulting mixture was heated to reflux for 2 hours. The volatiles were evaporated and the residue was dissolved in anhydrous THF (5 ml). TCDI (202 mg, 1.13 mmol) was added and the suspension was stirred at room temperature for 2 hours, partitioned between EtOAc (50 ml) and water (20 ml). The organic phase was separated, dried with anhydrous Na$_2$SO$_4$, filtered and concentrated. The residue was dissolved in THF (5 ml), BF$_3$-Et$_2$O was added and stirred at room temperature for 2 hours. Workup with 1N HCl, then the volatiles were evaporated and the residue was purified by prep-HPLC to afford the desired product in Example 11 (17.5 mg, 5%) as a white solid.

Data: $^1$HNMR (MeOD 500 MHz TMS): δ 8.04 (d, J=9.0 Hz, 1H), 8.01 (d, J=8.5 Hz, 2H), 7.45 (d, J=8.5 Hz, 2H), 7.04 (dd, J=1.5, 8.5 Hz, 1H), 6.90 (d, J=1.5 Hz, 1H); MS (ESI): m/z 406.9 [M+1]$^+$.

Example 12

3-(4-(1H-tetrazol-5-yl)phenyl)-7-hydroxy-2-methyl-4H-thiochromen-4-one

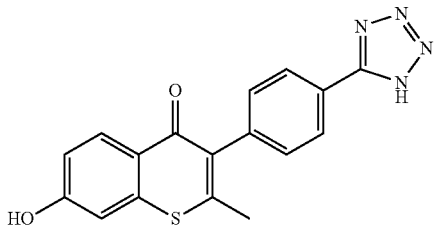 [SMILES: Cc1sc2cc(O)ccc2c(=O)c1-c1ccc(-c2nnn[nH]2)cc1]

Synthesis: Step 1: Synthesis of 4-(7-methoxy-2-methyl-4-oxo-4H-thiochromen-3-yl)benzonitrile: To a mixture of Intermediate G (664 mg, 2 mmol), 4-cyanophenylboronic acid (294 mg, 2 mmol) and TEA (1.4 ml, 10 mmol) in DMF (4 ml) was added Pd(dppf)Cl$_2$ (146 mg, 0.2 mmol) and the resultant mixture was heated to 85° C. under nitrogen for 18 hours. The mixture was cooled to room temperature, and then partitioned between 1N HCl (20 ml) and ethyl acetate (50 ml). The organic phase was separated, washed with brine (10 ml), dried over anhydrous Na$_2$SO$_4$ and concentrated, then purified by column chromatography (PE/EtOAc=5/1) to afford the product (310 mg, 54%) as a yellow solid.

Step 2: Synthesis of 4-(7-hydroxy-2-methyl-4-oxo-4H-thiochromen-3-yl)benzonitrile: To a solution of the above product (310 mg, 1.0 mmol) in DCM (3 ml) was added BBr$_3$ (1 ml, 10 mmol) carefully. The mixture was stirred at room temperature overnight. The resultant mixture was poured into icy water (5 ml), extracted with ethyl acetate (3 ml×3). The combined organic phase was washed with brine (3 ml), dried over anhydrous Na$_2$SO$_4$ and concentrated. Purification by column chromatography (PE/EtOAc=3/1) gave the product as a yellow powder (120 mg, 40%).

Step 3: Synthesis of Example 12: The tetrazole was then prepared from the above product following the method described in Example 1, Step 2 in 65% yield.

Data: $^1$HNMR (DMSO-d$_6$ 500 MHz TMS): δ 10.78 (s, 1H), 8.17 (d, J=9.0 Hz, 1H), 8.08 (d, J=8.0 Hz, 2H), 7.43 (d, J=8.0 Hz, 2H), 7.08 (s, 1H), 7.04 (d, J=9.0 Hz, 1H), 2.07 (s, 3H); MS (ESI): m/z 337.0 [M+1]$^+$.

Example 13

5-(7-hydroxy-4-oxo-2-(trifluoromethyl)-4H-chromen-3-yl)thiophene-3-carboxylic acid

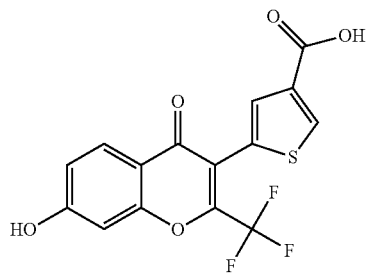 [SMILES: O=C(O)c1csc(-c2c(C(F)(F)F)oc3cc(O)ccc3c2=O)c1]

Synthesis: Step 1: Synthesis of methyl 5-(7-hydroxy-4-oxo-2-(trifluoromethyl)-4H-chromen-3-yl)thiophene-3-carboxylate: Followed the procedure described in Example 1, Step 1, where Intermediate H is the starting material and the crude product was purified by column chromatography to give the product in 43% yield.

Step 2: Synthesis of 5-(7-hydroxy-4-oxo-2-(trifluoromethyl)-4H-chromen-3-yl)thiophene-3-carboxylic acid: Followed the hydrolysis procedure described in Example 3, Step 2 to give the product in 65% yield.

Data: $^1$H NMR (MeOD-d$_4$ 500 MHz TMS): 8.42 (s, 1H), 8.05 (d, J=7.5 Hz, 1H), 7.48 (s, 1H), 7.05 (dd, J=2.5, 9.0 Hz, 1H), 6.96 (d, J=2.0 Hz, 1H); MS (ESI): m/z 357.0 [M−H]$^+$.

Example 14

3-((trans)-4-(1H-tetrazol-5-yl)cyclohexyl)-7-hydroxy-2-(trifluoromethyl)-4H-chromen-4-one

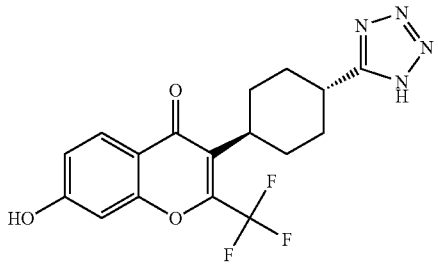 [SMILES: O=c1c2ccc(O)cc2oc(C(F)(F)F)c1[C@H]1CC[C@H](c2nnn[nH]2)CC1]

Synthesis: Step 1: Synthesis of (trans)-4-(7-hydroxy-4-oxo-2-(trifluoromethyl)-4H-chromen-3-yl)cyclohexanecarboxamide: Oxalyl chloride (6.5 ml, 84.27 mmol) was added drop wise to a solution of (trans)-4-(7-hydroxy-4-oxo-2-(trifluoromethyl)-4H-chromen-3-yl)cyclohexanecarboxylic acid (Example 3) (1.0 g) in DCM (25 ml) at room temperature (3 drops of DMF were added). Vigorous gas evolution was observed. After stirring for 30 minutes, NH$_3$H$_2$O (25%, 9 ml) was added to the above solution. After stirring for 60 minutes, ethyl acetate (50 ml) was added. The organic layer was concentrated and purified by column chromatography (PE/EtOAc=1/1) to give the desired product as a white solid (0.81 g, yield: 81%).

Step 2: Synthesis of (trans)-4-(7-hydroxy-4-oxo-2-(trifluoromethyl)-4H-chromen-3-yl)cyclohexanecarbonitrile: To a solution of the above product (0.81 g) and TEA (3.5 ml) in DCM (8.0 ml) was added drop wise TFAA (2.7 g) at room temperature. The mixture was stirred for 2 hours. The volatiles were removed in vacuo. The residue was purified by column chromatography (PE/EtOAc=5/1) to afford the product as a yellow solid (0.72 g, 74%).

Step 3: Synthesis of 3-((trans)-4-(1H-tetrazol-5-yl)cyclohexyl)-7-hydroxy-2-(trifluoromethyl)-4H-chromen-4-one: The tetrazole was prepared from the above product following the method described in Example 1, Step 2 in 59% yield.

Data: $^1$H NMR (MeOD-$d_4$ 500 MHz TMS): 7.87 (d, J=9.0 Hz, 1H), 6.86 (dd, J=2.0 Hz, J=9.0 Hz, 1H), 6.73 (d, J=2.5 Hz, 2H), 3.08-3.03 (m, 1H), 2.72 (t, J=12.5 Hz, 1H), 2.53-2.45 (m, 2H), 2.12 (d, J=12.0 Hz, 2H), 1.67-1.54 (m, 4H); MS (ESI): m/z 381.1 [M+1]$^+$.

Example 15

N-hydroxy-4-(7-hydroxy-4-oxo-2-(trifluoromethyl)-4H-chromen-3-yl)benzamide

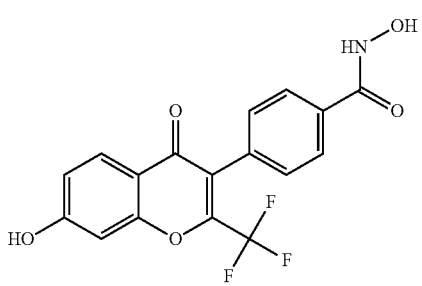 [SMILES: O=C(NO)c1ccc(-c2c(C(F)(F)F)oc3cc(O)ccc3c2=O)cc1]

Synthesis: Oxalyl chloride (140 mg, 1.1 mmol) was added dropwise to a solution of 4-(7-hydroxy-4-oxo-2-(trifluoromethyl)-4H-chromen-3-yl)benzoic acid (synthesis is described in PCT/US2010/024035) (130 mg, 0.4 mmol) and DMF (0.5 ml) in DCM (25 ml) at room temperature. Vigorous gas evolution was observed. After stirring for 30 minutes, the above solution was added to a mixture of hydroxylamine hydrochloride (0.29 g, 0.5 mmol) and TEA (0.12 ml, 0.9 mmol) in THF (2 ml) and water (0.5 ml). After stirring for 1 hour, the reaction mixture was extracted with EtOAc. The organic layer was washed with brine, dried over MgSO$_4$ and evaporated. The residue was recrystallized from acetone to give a white powder (120 mg), which was purified by prep-HPLC to afford desired product in Example 15 as a light yellow powder (48 mg, yield: 33%).

Data: $^1$H NMR (DMSO-$d_6$ 500 MHz TMS): 11.31 (s, 1H), 9.14 (s, 1H), 7.92 (t, J=4.5 Hz, 1H), 7.80 (s, 2H), 7.36 (d, J=3.5 Hz, 2H), 7.01 (d, J=5.5 Hz, 1H), 6.94 (s, 1H); MS (ESI): m/z 366.0 [M+1]$^+$.

Example 16

3-fluoro-4-(7-hydroxy-4-oxo-2-(trifluoromethyl)-4H-chromen-3-yl)benzoic acid

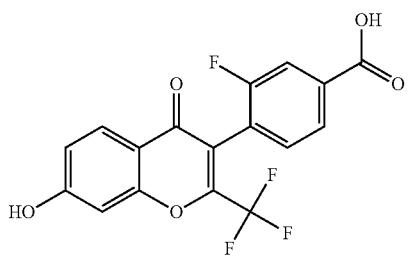 [SMILES: O=C(O)c1ccc(-c2c(C(F)(F)F)oc3cc(O)ccc3c2=O)c(F)c1]

Synthesis: Step 1: Synthesis of methyl 3-fluoro-4-(7-hydroxy-4-oxo-2-(trifluoromethyl)-4H-chromen-3-yl)benzoate: To a solution of methyl 4-(2-(2,4-dihydroxyphenyl)-2-oxoethyl)-3-fluorobenzoate (Intermediate I) (6 g, 19.7 mmol) in DCM (60 ml) and TEA (24 ml, 190 mmol) was added TFAA (13 ml, 95 mmol) drop wise. The mixture was stirred at room temperature for 15 hours. Then the solution was washed with 1 N HCl solution (50 ml) and water (50 ml); the organic layer was dried with Na$_2$SO$_4$, filtered and evaporated to give the crude product (6 g, 79.7%).

Step 2: To a solution of crude product from above (6 g, 15.7 mmol) in dioxane (60 ml) was added con. HCl (30 ml). The mixture was stirred at 90° C. for 15 hours. Then the solution was extracted by EtOAc (100 ml×5). The organic layers were combined, dried with Na$_2$SO$_4$, filtered and evaporated to give the crude product. The crude product was recrystallized by EtOAc/PE=3/1 (50 ml) to give the desired product in Example 16 (4.5 g, 77.9%) as a solid.

Data: $^1$H NMR (DMSO-$d_6$ 500 MHz TMS): δ 13.44 (brs, 1H), 11.31 (brs, 1H), 7.98 (d, J=9.0 Hz, 1H), 7.89 (dd, J=1.5 Hz, 7.5 Hz, 1H), 7.81 (dd, J=1.0 Hz, 9.5 Hz, 1H), 7.56 (t, J=8.0 Hz, 1H), 7.09 (dd, J=2.0 Hz, 8.5 Hz, 1H); 7.03 (d, J=2.0 Hz, 1H); MS (ESI): m/z 369.0 [M+1]$^+$.

Example 17

3-(2-chloro-4-(1H-tetrazol-5-yl)phenyl)-7-hydroxy-2-(trifluoromethyl)-4H-chromen-4-one

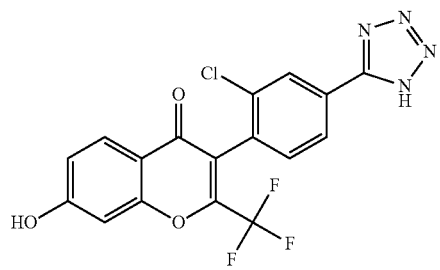 [SMILES: O=c1c(-c2ccc(-c3nnn[nH]3)cc2Cl)c(C(F)(F)F)oc2cc(O)ccc12]

Step 1: The desired product was synthesized by following the same 3 step procedure described for Example 14, starting from 3-chloro-4-(7-hydroxy-4-oxo-2-(trifluoromethyl)-4H-chromen-3-yl)benzoic acid (synthesis is described in PCT/US2010/024035).

Data: $^1$H NMR (MeOD-d$_4$ 500 MHz TMS): 8.22 (d, J=1.0 Hz, 1H), 8.07 (dd, J=1.5 Hz, J=8.0 Hz, 1H), 8.04 (d, J=9.0 Hz, 1H) 7.43 (d, J=8.5 Hz, 1H), 7.04 (dd, J=2.5 Hz, J=9.0 Hz, 1H), 6.98 (d, J=2.5 Hz, 1H); MS (ESI): m/z 409.0 [M+1]$^+$.

Example 18

3-(3-chloro-4-(7-hydroxy-4-oxo-2-(trifluoromethyl)-4H-chromen-3-yl)phenyl)-1,2,4-oxadiazol-5(4H)-one

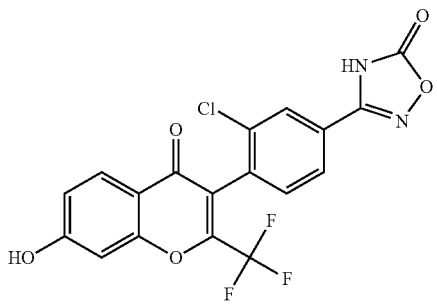 [SMILES: O=c1[nH]c(-c2ccc(-c3c(C(F)(F)F)oc4cc(O)ccc4c3=O)c(Cl)c2)no1]

Step 1 and 2: Synthesis of 3-chloro-4-(7-hydroxy-4-oxo-2-(trifluoromethyl)-4H-chromen-3-yl)benzonitrile: Followed the procedure described in the first two steps of Example 14, starting from 3-chloro-4-(7-hydroxy-4-oxo-2-(trifluoromethyl)-4H-chromen-3-yl)benzoic acid (synthesis is described in PCT/US2010/024035).

Step 3: 3-Chloro-4-(7-hydroxy-4-oxo-2-(trifluoromethyl)-4H-chromen-3-yl)benzonitrile (0.3 g, 0.8 mmol) was dissolved in EtOH (5 ml) and cooled with an ice bath. Hydroxyamine HCl salt (46 mg, 0.85 eq.) and TEA (0.11 ml, 1 eq.) were added. The reaction mixture was stirred overnight at room temperature. The solvent was removed and the residue (0.4 g) was suspended in anhydrous THF (5 ml). After addition of CDI (0.24 g, 1.5 eq.) and TEA (0.13 ml), the suspended solution was stirred and heated at 50° C. overnight. After removal of THF, the mixture was suspended in water (15 ml) and the pH was adjusted to 8. The aqueous layer was extracted with EtOAc (10 ml×2). Then, the aqueous layer was acidified to pH ~2 and was extracted with EtOAc (15 ml×4). The combined organic layers were washed with brine and dried over anhydrous Na$_2$SO$_4$. After removal of the solvent, the crude product was purified by prep-HPLC to afford desired product in Example 18 (44 mg, 10%) as tan solid.

Data: $^1$H NMR (MeOH-d$_4$ 500 MHz TMS): 8.04 (d, J=8.5 Hz, 1H), 7.99 (d, J=1.5 Hz, 1H), 7.84 (dd, J=1.5 Hz, 8.0 Hz, 1H), 7.53 (d, J=8.5 Hz, 1H), 7.06 (dd, J=2.0 Hz, 8.5 Hz, 1H), 6.98 (d, J=2.0 Hz, 1H); MS (ESI): m/z 425 [M+1]$^+$.

Example 19

3-(3-fluoro-4-(7-hydroxy-4-oxo-2-(trifluoromethyl)-4H-chromen-3-yl)phenyl)-1,2,4-oxadiazol-5(4H)-one

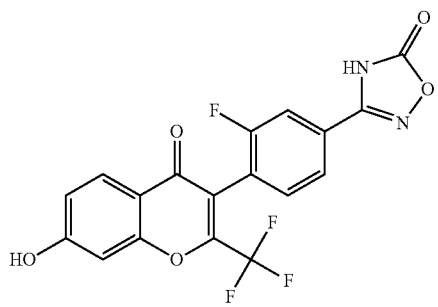 [SMILES: O=c1[nH]c(-c2ccc(-c3c(C(F)(F)F)oc4cc(O)ccc4c3=O)c(F)c2)no1]

Synthesis: 3-fluoro-4-(7-hydroxy-4-oxo-2-(trifluoromethyl)-4H-chromen-3-yl)benzonitrile was prepared according to the first two steps of Example 14 starting from 3-fluoro-4-(7-hydroxy-4-oxo-2-(trifluoromethyl)-4H-chromen-3-yl)benzoic acid (Example 16), and then converted to desired product in Example 19 following Step 3 of Example 18.

Data: $^1$H NMR (MeOH-d$_4$ 500 MHz TMS): 8.06 (d, J=9.0 Hz, 1H), 7.75 (dd, J=2.0 Hz, 8.0 Hz, 2H), 7.70 (dd, J=2 Hz, 10.0 Hz, 1H), 7.54 (t, J=7.5 Hz, 1H), 7.07 (dd, J=2.5 Hz, 9.0 Hz, 1H), 7.00 (d, J=2.0 Hz, 1H); MS (ESI): m/z 409 [M+1]$^+$.

Example 20

3-(3-chloro-4-(1H-tetrazol-5-yl)phenyl)-7-hydroxy-2-(trifluoromethyl)-4H-chromen-4-one

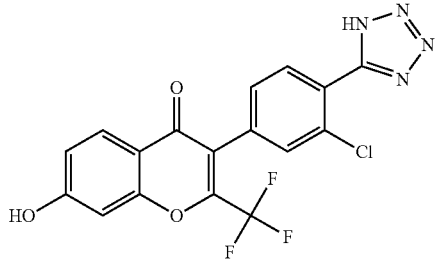 [SMILES: O=c1c(-c2ccc(-c3nnn[nH]3)c(Cl)c2)c(C(F)(F)F)oc2cc(O)ccc12]

Synthesis: 2-chloro-4-(7-hydroxy-4-oxo-2-(trifluoromethyl)-4H-chromen-3-yl)benzonitrile was prepared according to the first two steps of Example 14 starting from 2-chloro-4-(7-hydroxy-4-oxo-2-(trifluoromethyl)-4H-chromen-3-yl)benzoic acid (synthesis is described in PCT/US2010/024035), and then converted to desired product in Example 20 following the procedure described in Example 1, Step 2.

Data: $^1$H NMR (MeOD-d$_4$ 500 MHz TMS): 8.07 (d, J=9.0 Hz, 1H), 7.95 (d, J=8.0 Hz 1H), 7.65 (s, 1H), 7.48 (d, J=8.0

Hz, 1H), 7.07 (dd, J=2.0 Hz, J=9.0 Hz, 1H), 6.98 (d, J=2.0 Hz, 1H); MS (ESI): m/z 409.0 [M+1]⁺.

Example 21

4-(7-hydroxy-4-oxo-2-(trifluoromethyl)-4H-chromen-3-yl)-3-methylbenzoic acid

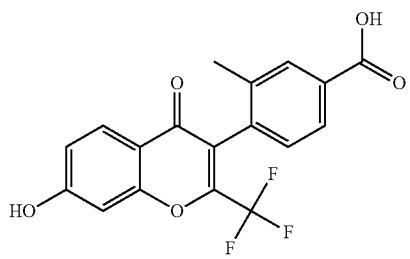

Synthesis: Desired product was synthesized by following a similar two step procedure to that described in Example 16, starting from methyl 4-(2-(2,4-dihydroxyphenyl)-2-oxoethyl)-3-methylbenzoate (Intermediate J).

Data: $^1$H NMR (DMSO-d$_6$, 300 MHz): δ 13.02 (brs, 1H), 11.21 (brs, 1H), 7.95 (d, J=9.0 Hz, 1H), 7.88 (d, J=3 Hz, 1H), 7.80 (dd, J=3, 9 hz, 1H), 7.30 (d, J=9 Hz, 1H), 7.04 (dd, J=3, 9 Hz, 1H), 7.00 (d, J=3 Hz, 1H), 2.13 (s, 3H); MS (ESI): m/z 365.1 [M+H⁺]⁺.

Example 22

3-(4-(1H-tetrazol-5-yl)phenyl)-7-hydroxy-4H-chromen-4-one

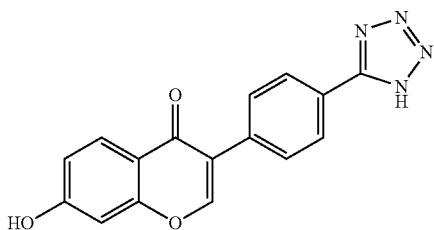 [SMILES: O=c1c(-c2ccc(-c3nnn[nH]3)cc2)coc2cc(O)ccc12]

Step 1: Synthesis of 4-(7-hydroxy-4-oxo-4H-chromen-3-yl)benzonitrile: To a solution of Intermediate K (200 mg, 0.79 mmol) in anhydrous DMF (6.0 ml) was added dropwise BF$_3$-Et$_2$O (0.8 ml) at 0~10° C. When the addition was complete, the mixture was allowed to warm to room temperature for 0.5 hours, heated to 90° C. MsCl (1.6 ml) was added in one portion and stirred for 5 hours. The mixture was partitioned between EtOAc (50 ml) and 1N HCl (50 ml). The organic phase was separated, dried with anhydrous sodium sulfate, filtered and concentrated to afford light yellow solid, which was recrystallized from DCM (5 ml) to afford the product (120 mg, 58%) as a yellow solid. MS (ESI): m/z 263.9 [M+1]⁺.

Step 2: Synthesis of 3-(4-(1H-tetrazol-5-yl)phenyl)-7-hydroxy-4H-chromen-4-one: Followed the procedure described for step 2 of Example 1, where the product was recrystallized twice from DCM (10 ml) to afford desired product in Example 22 as a white solid (60 mg, 43%).

Data: $^1$HNMR (DMSO-d$_4$ 500 MHz TMS): δ 10.89 (s, 1H), 8.54 (d, J=8.5 Hz, 1H), 8.08 (d, J=8.5 Hz, 2H), 8.01 (m, 1H), 7.79 (d, J=8.0 Hz, 1H), 6.98 (dd, J=2.5, 8.0 Hz, 1H), 6.91 (d, J=2.0 Hz, 1H); MS (ESI): m/z 307.1 [M+1]⁺.

Example 23

5-(4-(7-hydroxy-4-oxo-2-(trifluoromethyl)-4H-chromen-3-yl)phenyl)-1,3,4-oxadiazol-2(3H)-one

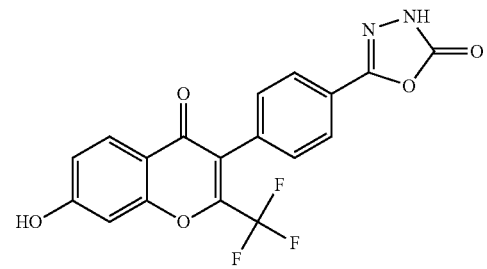 [SMILES: O=c1[nH]nc(-c2ccc(-c3c(C(F)(F)F)oc4cc(O)ccc4c3=O)cc2)o1]

Synthesis: Example 23 can be prepared according to the following three step procedure:

Step 1: Synthesis of tert-butyl 2-(4-(7-hydroxy-4-oxo-2-(trifluoromethyl)-4H-chromen-3-yl)benzoyl)hydrazinecarboxylate: A mixture of 4-(7-hydroxy-4-oxo-2-(trifluoromethyl)-4H-chromen-3-yl)benzoic acid (synthesis is described in PCT/US2010/024035) (1 equiv.), EDCI (1 equiv.), and BocNHNH$_2$ (1 equiv.), in DCM and DMF (1:1) is stirred at 25° C. overnight, followed by an aqueous/EtOAc workup. Purification if necessary by column chromatography on silica gel to give the product.

Step 2: Synthesis of 4-(7-hydroxy-4-oxo-2-(trifluoromethyl)-4H-chromen-3-yl)benzohydrazide: tert-Butyl 2-(4-(7-hydroxy-4-oxo-2-(trifluoromethyl)-4H-chromen-3-yl)benzoyl)hydrazinecarboxylate is treated with HCl/MeOH overnight. Solvent is removed under reduced pressure to give the product.

Step 3: Synthesis of 5-(4-(7-hydroxy-4-oxo-2-(trifluoromethyl)-4H-chromen-3-yl)phenyl)-1,3,4-oxadiazol-2(3H)-one: 4-(7-hydroxy-4-oxo-2-(trifluoromethyl)-4H-chromen-3-yl)benzohydrazide (1 equiv.) and CDI (10 equiv.) in DCM is refluxed overnight. An aqueous/EtOAc workup followed by purification by prep-HPLC can give the desired product in Example 23.

Example 24

4-(8-fluoro-7-hydroxy-4-oxo-2-(trifluoromethyl)-4H-chromen-3-yl)benzoic acid

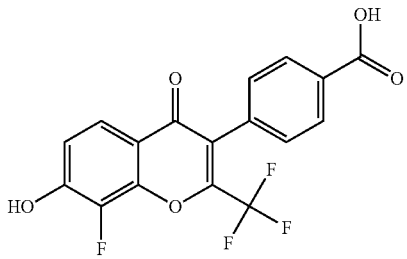 [SMILES: O=C(O)c1ccc(-c2c(C(F)(F)F)oc3c(F)c(O)ccc3c2=O)cc1]

Synthesis: Desired product in Example 24 can be prepared following the two step procedure described for Example 16 starting from methyl 4-(2-(3-fluoro-2,4-dihydroxyphenyl)-2-oxoethyl)benzoate (Intermediate L).

Example 25

Synthesis of Intermediates

The intermediates referenced in the above examples can be synthesized as described below.

Intermediate A 4-(2-(2,4-dihydroxyphenyl)-2-oxoethyl)benzamide

Step 1: Synthesis of 2-(4-(methoxycarbonyl)phenyl)acetic acid. To a solution of 2-(4-bromophenyl)acetic acid (91.3 g, 0.42 mol, 1.0 eq.) in MeOH (1.5 L) was added dry TEA (85.8 g, 0.85 mol, 2.0 eq.) and Pd(dppf)Cl$_2$ (3.43 g, 4.2 mmol, 1%). The solution was heated under CO gas (4 MPa) at 120° C. for 16 hours. Then it was filtered and concentrated in vacuo. The residue was dissolved in 500 ml of EtOAc and 1 L of water. The mixture was neutralized by sat. NaHCO$_3$ to pH=7.5 and separated. The inorganic phase was extracted with EtOAc (500 ml×3) acidified with 1N HCl to pH=5. Filtration and drying in vacuo afforded 62.8 g of product (white solid, yield 76%). MS (ESI): m/z 195.1 [M+1]$^+$.

Step 2: Synthesis of methyl 4-(2-(2,4-dimethoxyphenyl)-2-oxoethyl)benzoate. To a solution of 2-(4-(methoxycarbonyl)phenyl)acetic acid (15 g, 77.3 mmol) and DMF (1 drop) in anhydrous DCM (150 ml) was added dropwise oxalyl chloride (33 ml, 386.0 mmol) at 0~5° C. with stirring. After the addition was complete, the mixture was stirred at room temperature for 2 hours. TLC (PE/EtOAc=3/1, quenched with MeOH) indicated that the reaction was complete, the volatiles were evaporated and the residue was diluted with DCM (20 ml).

To a suspension of aluminum trichloride (16.5 g, 123.7 mmol) in anhydrous DCM (80 ml) was added 1,3-dimethoxybenzene (21.3 g, 154.6 mmol) at 5° C., followed by above acyl chloride solution. The mixture was stirred at room temperature overnight, poured carefully into icy 1 N HCl (200 ml) and extracted with EtOAc (150 ml×3). The combined organic layers were washed with brine (200 ml), dried with anhydrous sodium sulfate, filtered and concentrated to obtain brown oil, which was purified by silica gel column (PE/EtOAc=5/1) to afford product (12 g, 49.6%) as a yellow solid. MS (ESI): m/z 315.1 [M+1]$^+$.

Step 3: Synthesis of ethyl 4-(2-(2,4-dihydroxyphenyl)-2-oxoethyl)benzoate. To a solution of methyl 4-(2-(2,4-dimethoxyphenyl)-2-oxoethyl)benzoate (55 g, 141.6 mmol) in DCM (600 ml) was added dropwise BBr$_3$ (164 ml, 1.7 mol) at −10° C. When the addition was complete, the mixture was stirred at room temperature overnight and poured into crashed ice (700 g) with stirring. The volatiles were evaporated to afford a yellow solid, which was dried in high vacuo and dissolved in absolute ethanol (500 ml). To the solution was added dropwise thionyl chloride (80 ml) at 0~10° C. When the addition was complete, the resultant mixture was heated to reflux for 3 hours. The volatiles were evaporated and the residue was partitioned between EtOAc (600 ml) and saturated sodium carbonate (200 ml). The organic phase was separated, washed with brine (200 ml), dried with anhydrous sodium sulfate, filtered and concentrated to afford brown slurry, which was purified by column chromatography (PE/EtOAc=3/1) to afford product (24.5 g, 58%) as a yellow solid.

$^1$H NMR (CDCl$_3$ 500 MHz TMS): δ 12.58 (s, 1H), 8.01 (d, J=8.5 Hz, 2H), 7.69 (d, J=9.0 Hz, 1H), 7.33 (d, J=8.0 Hz, 2H), 7.05 (brs, 1H), 6.41 (d, J=8.0 Hz, 1H), 6.37 (s, 1H), 4.38 (q, J=7.0 Hz, 2H), 4.26 (s, 2H), 1.38 (t, J=7 Hz, 3H). MS (ESI): m/z 301.1 [M+1]$^+$.

Step 4: Synthesis of 4-(2-(2,4-dihydroxyphenyl)-2-oxoethyl)benzoic acid. To a solution of ethyl 4-(2-(2,4-dihydroxyphenyl)-2-oxoethyl)benzoate (2 g, 6.7 mmol) in 1,4-dioxane (10 ml), was added conc. HCl (10 ml). The reaction mixture was stirred at 70° C. overnight. The volatiles were removed under reduced pressure. The residue was dissolved with water (20 ml) and extracted with EtOAc (20 ml×2). The combined organic phase was dried over anhydrous Na$_2$SO$_4$, filtered and concentrated to afford product as a brown solid (1.5 g, 83.3%). MS (ESI): m/z 273.1 [M+1]$^+$.

Step 5: Synthesis of 4-(2-(2,4-dihydroxyphenyl)-2-oxoethyl)benzamide. To a solution of 4-(2-(2,4-dihydroxyphenyl)-2-oxoethyl)benzoic acid (1.5 g, 5.5 mmol) in DCM (20 ml) was added oxalyl chloride (4.7 ml, 55 mmol) and one drop of DMF. The mixture was stirred at room temperature for 3 h and then the mixture was refluxed overnight. The mixture was concentrated to dryness. The residue was dissolved in THF (20 ml). Then it was added drop wise into aq. NH$_3$.H$_2$O (25%, 60 ml) at the room temperature. The mixture was stirred at room temperature for 2 hours. The volatiles were removed under reduced pressure. The residue was extracted with EtOAc (30 ml×3). The combined organic phase was dried over Na$_2$SO$_4$ and concentrated to afford product as brown solid (300 mg, 20.1%). MS (ESI): m/z 272.1[M+1]+.

Intermediate B methyl 5-(2-(2,4-dihydroxyphenyl)-2-oxoethyl)thiophene-2-carboxylate Step 1: Synthesis of 2-(5-bromothiophen-2-yl)acetic acid. To a solution of 2-(thiophen-2-yl)acetic acid (2 g, 14 m mol) in HOAc (10 ml) was added dropwise bromine (2.25 g, 14 mmol) at 10~20° C. for 30 min. The mixture was allowed to warm to room temperature for 3 hours. Then it was diluted with water (100 ml), neutralized to pH=5 with anhydrous sodium carbonate and extracted with EtOAc (100 ml×3). Dried over Na$_2$SO$_4$, filtered and concentrated to afford crude product as brown oil. MS (ESI): m/z 220.9 [M+1]$^+$.

Step 2: Synthesis of 2-(5-(methoxycarbonyl)thiophen-2-yl)acetic acid: To a solution of 2-(5-bromothiophen-2-yl)acetic acid (2.5 g, 11.4 mmol) in MeOH (110 ml) was added TEA (5 ml, 34.1 mmol) and Pd(dppf)Cl$_2$ (769 mg, 1.1 mmol) and the resultant mixture was heated at 120° C. under CO (4 MPa) for 20 hours. Concentration in vacuo and the residue was purified by Combi-Flash (80 g silica gel, start PE/EtOAc=10:0 to 1:3 gradient, 60 ml/min, 60 min, 3.6 L total solvent volume) to afford product as a light solid (1.3 g, 58%). MS (ESI): m/z 198.0 [M+1]$^+$.

Step 3: Synthesis of methyl 5-(2-(2,4-dimethoxyphenyl)-2-oxoethyl)thiophene-2-carboxylate. Prepared following procedure described in Step 2 of Intermediate A, starting with 2-(5-(methoxycarbonyl)thiophen-2-yl)acetic acid.

Step 4: Synthesis of methyl 5-(2-(2,4-dihydroxyphenyl)-2-oxoethyl)thiophene-2-carboxylate. To a solution of methyl 5-(2-(2,4-dimethoxyphenyl)-2-oxoethyl)thiophene-2-carboxylate (460 mg, 1.44 mmol) in DCM (5 ml) was added AlCl$_3$ (5.7 g, 43 mmol). The mixture was stirred at room temperature for two days. Water (15 ml) was added carefully at 0° C. and the mixture was extracted with EtOAc (20 ml×3). The combined organic phase was washed with brine (50 ml), dried over Na$_2$SO$_4$, concentrated and purified by prep-TLC (PE/EtOAc=3/1) to afford Intermediate B as an orange powder (260 mg, 61.9%). MS (ESI): m/z 293.0 [M+1]$^+$.

Intermediate C ethyl 4-(2-(2,4-dihydroxyphenyl)-2-oxoethyl)cyclohexanecarboxylate Step 1: Synthesis of ethyl 4-(2-tert-butoxy-2-oxoethylidene)cyclohexanecarboxylate. To a suspension of anhydrous lithium chloride (1.9 g, 45 mmol) in MeCN (100 ml) was added tert-butyl 2-(diethoxyphosphoryl)acetate (7.6 g, 30 mmol) at room temperature. The mixture was stirred for 30 min. TEA (6.4 ml, 45 mmol) was added and the mixture was stirred for another 30 min. Ethyl 4-oxocyclohexanecarboxylate (5.1 g, 30 mmol) was added and the mixture was stirred overnight. The precipitate was filtered off and the filtrate was concentrated to afford brown oil, which was purified by silica gel column (PE:EtOAc=10:1) to afford product (5 g, 62%).

Step 2: Synthesis of 2-(4-(ethoxycarbonyl)cyclohexylidene)acetic acid. To a solution of ethyl 4-(2-tert-butoxy-2-oxoethylidene)cyclohexanecarboxylate (5.3 g, 21 mmol) in CH$_2$Cl$_2$ (30 ml) was added TFA (30 ml). The solution was stirred at room temperature overnight. The solution was concentrated in vacuo to afford 6 g of product as colorless oil, which was used directly for next step without further purification.

Step 3: Synthesis of 2-(4-(ethoxycarbonyl)cyclohexyl)acetic acid. To a solution of 2-(4-(ethoxycarbonyl)cyclohexylidene)acetic acid (6.0 g, 28.3 mmol) in EtOH (50 ml) was slowly added 10% Pd/C (306 mg). The solution was hydrogenated overnight. The catalyst was filtered off. The filtrate was concentrated in vacuo to afford 2.5 g of product as colorless oil (42%).

Step 4: Synthesis of ethyl 4-(2-(2,4-dihydroxyphenyl)-2-oxoethyl)cyclohexanecarboxylate (Intermediate C). To a solution of 2-(4-(ethoxycarbonyl)cyclohexyl)acetic acid (700 mg, 11.6 mmol) in BF$_3$-Et$_2$O (10 ml) was added resorcinol (1.5 g, 14.0 mmol). The solution was stirred at 85° C. overnight, poured into Na$_2$CO$_3$ solution (2N, 20 ml), extracted with EtOAc (30 ml×3), washed with brine, dried over Na$_2$SO$_4$, filtrated and concentrated to afford 3 g of yellow oil, which was purified by silica gel column (PE/EtOAc=3/1) to afford 400 mg of Intermediate C. MS (ESI): m/z 307.1[M+1]$^+$.

Intermediate D 2-(4-(2H-tetrazol-5-yl)phenyl)-1-(2,4-dihydroxyphenyl)ethanone

Step 1: Synthesis of 2-(4-bromophenyl)-1-(2,4-dihydroxyphenyl)ethanone. Followed Step 4 of Intermediate C, starting with 2-(4-bromophenyl)acetic acid to give product as an orange powder (20 g, 27.9%). MS (ESI): m/z 307.0, 309.0 [M+1]$^+$, [M+3]$^+$.

Step 2: Synthesis of 4-(2-(2,4-dihydroxyphenyl)-2-oxoethyl)benzonitrile. A mixture of 2-(4-bromophenyl)-1-(2,4-dihydroxyphenyl)ethanone (5 g, 16.3 mmol) and CuCN (5.8 g, 65.4 mmol) in DMF (50 ml) was stirred at 150° C. for 6 h under nitrogen. Water (100 ml) and EtOAc (100 ml) was added to the mixture. The precipitate was filtered off and the filtrate was washed with brine (100 ml), dried over Na$_2$SO$_4$ and concentrated to give black oil, which was purified by Combiflash (PE/EtOAc=3/1) to afford product as a yellow powder (1.5 g, 36.6%). MS (ESI): m/z 254.1 [M+1]$^+$.

Step 3: Synthesis of 2-(4-(2H-tetrazol-5-yl)phenyl)-1-(2,4-dihydroxyphenyl)ethanone. To a solution of 4-(2-(2,4-dihydroxyphenyl)-2-oxoethyl)benzonitrile (1.2 g, 4.7 mmol) in toluene (15 ml) was added TMSN$_3$ (9.3 g, 85.4 mmol) and Bu$_2$SnO (309 mg, 1.41 mmol) at room temperature. The mixture was heated to reflux overnight. The volatiles were removed under reduced pressure and the residue was purified by Combiflash (EtOAc/HOAc=50/1) to afford Intermediate D as a yellow powder (550 mg, 39.6%). $^1$H NMR (DMSO-d$_6$ 500 MHz TMS): δ 12.41 (s, 1H), 10.72 (s, 1H), 7.99~7.96 (m, 3H), 7.51 (d, J=8.0 Hz, 2H), 6.42 (dd, J=2.0 Hz, J=9.0 Hz, 1H), 6.27 (d, J=2.5 Hz,1H), 4.44 (s, 2H); MS (ESI): m/z 297.0 [M+1]$^+$.

Intermediate E methyl 4-(2-(3-methoxyphenylthio)-2-oxoethyl)benzoate

To a solution of 2-(4-(methoxycarbonyl)phenyl)acetic acid (see Intermediate A, step 1 for synthesis) (3.88 g, 20 mmol) in dry DCM (50 ml) was added dropwise oxalyl chloride (8.4 ml, 100 mmol) at room temperature with stirring. The mixture was stirred at room temperature for 2 hours. The reaction was complete indicated by TLC (PE:EtOAc=3:1, quenched with MeOH). The mixture was concentrated to afford methyl 4-(2-chloro-2-oxoethyl)benzoate (4.5 g) as yellow oil, which was used directly for next step.

To a suspension of aluminum trichloride (2.93 g, 21.96 mmol) in dry CS$_2$ (50 ml) was added 3-methoxybenzenethiol (3.1 g, 21.96 mmol) at 0~5° C., followed by a solution of methyl 4-(2-chloro-2-oxoethyl)benzoate (4.5 g, crude, 21.16 mmol) in dry CS$_2$ (5 ml). The mixture was stirred at room temperature overnight and poured carefully into 1 N icy HCl (200 ml) and extracted with EtOAc (100 ml×3). The combined organic layers were washed with water (100 ml×2) and brine (100 ml), dried over Na$_2$SO$_4$, filtered and concentrated. The residue was purified by Combi-Flash (80 g silica gel, start PE/EtOAc=10/0 to 1/1 gradient, 50 ml/min, 40 min, 2.0 L total solvent volume) to afford Intermediate E as a yellow solid (2.7 g, 43%). $^1$H NMR (DMSO-d6 500 MHz TMS): δ 7.95 (d, J=8.5 Hz, 2H), 7.49 (d, J=8.5 Hz, 2H), 7.37 (d, J=8.0 Hz, 1H), 7.02~7.04 (m, 1H), 6.97~6.98 (m, 2H), 4.18 (s, 2H), 3.85 (s, 3H), 3.76 (s, 3H); MS (ESI): m/z 317.1 [M+1]$^+$.

Intermediate F methyl 4-(2-(2-(acetylthio)-4-methoxyphenyl)-2-oxoethyl)benzoate

Step 1: Synthesis of S-3-methoxyphenyl ethanethioate. To a solution of 3-methoxybenzenethiol (5 g, 35.66 mmol) and TEA (7.45 ml, 53.49 mmol) in DCM (60 ml) was added Ac$_2$O (4 g, 39.23 mmol) at room temperature and stirred for 3 hours. The reaction mixture was washed with 1 N HCl (50 ml×2), water (50 ml×2) and brine (50 ml), dried with anhydrous sodium sulfate, filtered and concentrated to afford product as a yellow solid (6.5 g, 100%). MS (ESI): m/z 183.1 [M+1]$^+$.

Step 2: Synthesis of methyl 4-(2-chloro-2-oxoethyl)benzoate. To a solution of 2-(4-(methoxycarbonyl)phenyl)acetic acid (see Intermediate A, step 1 for synthesis) (5 g, 25.75 mmol) in DCM (60 ml) was added dropwise oxalyl chloride (6.6 ml, 77.25 mmol) at room temperature and the mixture was stirred for 4 hours. Concentration afforded product as golden oil (6 g, 109%), which was used directly for next step.

Step 3: Synthesis of methyl 4-(2-(2-(acetylthio)-4-methoxyphenyl)-2-oxoethyl)benzoate (Intermediate F). To a suspension of aluminum trichloride (9.9 g, 74.08 mmol) in DCM (100 ml) was added S-3-methoxyphenyl ethanethioate (step 1) (4.5 g, 30.57 mmol) at 0~5° C., followed by a solution of methyl 4-(2-chloro-2-oxoethyl)benzoate (step 2) (4.5 g, crude, 24.69 mmol) in DCM (20 ml). The mixture was stirred at room temperature for 3 days. The mixture was poured carefully into icy 1 N HCl (200 ml) and extracted with EtOAc (50 ml×2). The combined organic layers were washed with water (100 ml×2) and brine (100 ml), dried with anhydrous sodium sulfate, filtered and concentrated. The residue was purified by column chromatography (PE/EtOAc=15/1 to 10/1) to afford Intermediate F as a yellow solid (1.8 g, 14%). MS (ESI): m/z 359.0 [M+1]$^+$.

Intermediate G 3-iodo-7-methoxy-2-methyl-4H-thiochromen-4-one

Step 1: Synthesis of 7-methoxy-2-methyl-4H-thiochromen-4-one: To a mixture of 3-methoxybenzenethiol (24 g, 28.5 mmol) in PPA (200 g) was added ethyl acetoacetate (22.8 g, 28.5 mmol) at room temperature under nitrogen. Then the reaction mixture was heated to 110° C. for 5 h with vigorous stirring and poured into ice-water (100 ml). The resultant mixture was extracted with ethyl acetate (500 ml×3). The combined organic phase was dried with anhydrous sodium sulfate, filtered and concentrated, then purified by silica gel column (PE/EtOAc=10/1) to afford desired product (2 g, 4%) as a yellow solid.

Step 2: Synthesis of 3-iodo-7-methoxy-2-methyl-4H-thiochromen-4-one: To a solution of 7-methoxy-2-methyl-4H-thiochromen-4-one (500 mg, 2.42 mmol) and iodine (620 mg, 2.42 mmol) in anhydrous acetonitrile (10 ml) was added CAN (1.5 g, 2.70 mmol) at room temperature. Then the mixture was stirred for 5 h under nitrogen. The volatiles were evaporated in vacuo and the residue was partitioned between ethyl acetate (20 ml) and saturated $Na_2S_2O_3$ (20 ml). The organic phase was separated, dried with anhydrous sodium sulfate, filtered and concentrated to obtain a yellow solid, which was recrystallized from methanol (5 ml) to afford Intermediate G (620 mg, 77%) as a light yellow solid. $^1$HNMR (CDCl$_3$ 500 MHz): δ 8.46 (d, J=9.0 Hz, 1H), 7.09 (dd, J=2.5, 9.5 Hz, 1H), 6.94 (d, J=2.5 Hz, 1H), 3.90 (s, 3H), 2.61 (s, 3H).

Intermediate H methyl 5-(2-(2,4-dihydroxyphenyl)-2-oxoethyl)thiophene-3-carboxylate Step 1: Synthesis of methyl 2-(4-bromothiophen-2-yl)acetate: To a solution of methyl 2-(thiophen-2-yl)acetate (5 g, 32 mmol) and anhydrous AlCl$_3$ (10.7 g, 80 mmol) in CHCl$_3$ (50 ml) was added dropwise bromine (1.8 ml, 34 mmol) at 0~5° C. over 30 min. When the addition was complete, the mixture was allowed to warm to room temperature overnight. Then it was poured into icy water (50 ml), extracted with EtOAc (30 ml×3). The combined organic phase was dried over Na$_2$SO$_4$, filtered and concentrated. Purification by column chromatography (PE/EtOAc=10/1) gave the product (3.1 g, 41%) as light yellow oil.

Step 2: Synthesis of methyl 5-(2-methoxy-2-oxoethyl)thiophene-3-carboxylate: To a solution of the above product (3.1 g, 13.4 mmol) in MeOH (110 ml) was added TEA (10 ml, 67.0 mmol) and Pd(dppf)Cl$_2$ (976 mg, 1.4 mmol) and the resultant mixture was heated at 120° C. under CO (4 MPa) for 20 hours. Concentration and the residue was partitioned between ethyl acetate (50 ml) and 1 N HCl (20 ml). The organic phase was separated, dried with anhydrous sodium sulfate, filtered and concentrated to give the product.

Step 3: Synthesis of 2-(4-(methoxycarbonyl)thiophen-2-yl)acetic acid: To a solution of the above product (2.8 g, 13.1 mmol) in THF/H$_2$O (15/15 ml) was added lithium hydroxide monohydrate (490 mg, 11.7 mmol) by 3 portions at room temperature. The mixture was stirred for 2 days and extracted with PE (10 ml). The aqueous phase was separated, acidified with pH=5 with 1N HCl, extracted with EtOAc (30 ml×3). The combined organic phase was dried with anhydrous sodium sulfate, filtered and concentrated to give the crude product.

Step 4: Synthesis of Intermediate H: To a mixture of the above product (450 mg, 2.3 mol) and resorcinol (248 mg, 2.3 mol) was added BF$_3$-Et$_2$O (2 ml) and the mixture was stirred at 95° C. overnight. The mixture was poured into saturated sodium carbonate (10 ml) until pH=10, and extracted with ethyl acetate (20 ml×3). The combined organic phase was separated, dried over anhydrous sodium sulfate, filtered and concentrated to give yellow oil, which was purified by column chromatography (PE/EtOAc=3/1) to afford Intermediate H as a yellow solid (95 mg, 15%). MS (ESI): m/z 292.9 [M+1]$^+$.

Intermediate I methyl 4-(2-(2,4-dihydroxyphenyl)-2-oxoethyl)-3-fluorobenzoate

Step 1: Synthesis of methyl 3-fluoro-4-methylbenzoate: A solution of 3-fluoro-4-methylbenzoic acid (20 g, 130 mmol) in thionyl chloride (80 ml) was heated to reflux for 2 h (TLC showed that there is no start material) and the volatiles were evaporated. To the residue was added MeOH (100 ml) drop wise at 0° C. with stirring. The mixture was stirred at room temperature for 1 hours. The reaction was concentrated and diluted with EtOAc and washed with brine. The organic layer was dried with anhydrous Na$_2$SO$_4$, filtered and evaporated to afford the product as a white solid and used without further purification for the next step. (21 g, 96%).

Step 2: Synthesis of methyl 4-(bromomethyl)-3-fluorobenzoate: To a solution of the above product (21 g, 125 mmol) in CCl$_4$ (200 ml) was added a mixture of NBS (20 g, 113 mmol) and benzoyl peroxide (1.5 g, 6 mmol). The resulting solution was refluxed for 5 hours. Then the solvent was evaporated and the residue was dissolved in DCM (300 ml) and washed with H$_2$O (200 ml×3). The organic layer was dried with anhydrous Na$_2$SO$_4$, filtered and evaporated to give the crude product as colorless oil (18 g, 64.7%).

Step 3: Synthesis of methyl 4-(cyanomethyl)-3-fluorobenzoate: To a solution of methyl 4-(bromomethyl)-3-fluorobenzoate (18 g, 73 mmol) in MeOH (150 ml) was added the solution of NaCN (7.2 g, 146 mmol) in H$_2$O (40 ml). The mixture was stirred at 65° C. for 5 hours. Most of MeOH was evaporated and additional water was added and extracted by EtOAc (200 ml×3), dried with anhydrous Na$_2$SO$_4$, filtered and evaporated to give the crude product. Purification by column chromatography (PE/EtOAc=50/1 to 10/1) gave the product (8 g, 63.8%).

Step 4: Synthesis of methyl 4-(2-(2,4-dihydroxyphenyl)-2-oxoethyl)-3-fluorobenzoate: To a solution of methyl 4-(cyanomethyl)-3-fluorobenzoate (8 g, 41 mmol) and resorcinol (6.8 g, 62 mmol) in BF$_3$-Et$_2$O (100 ml) was bubbled with HCl at 0° C. for 15 min. The mixture was stirred at 75° C. for 16 hours. Then H$_2$O (100 ml) was added and the solution was heated at 95° C. for 16 hours. The mixture was cooled to room temperature and neutralized by Na$_2$CO$_3$ and extracted with EtOAc (100 ml×3). The organic layers were combined, dried with anhydrous $Na_2SO_4$, filtered and evaporated to give the crude product. Purification by column chromatography (PE/EtOAc=10/1 to 3/1) gave Intermediate I as a white solid (6 g, 48%).

Intermediate J methyl 4-(2-(2,4-dihydroxyphenyl)-2-oxoethyl)-3-methylbenzoate

Step 1: Synthesis of methyl 4-(2-ethoxy-2-oxoethyl)-3-methylbenzoate: Methyl 4-bromo-3-methylbenzoate (1.5 g, 6.55 mmol), methyl 3-oxobutanoate (0.99 g, 8.51 mmol) and $K_3PO_4$ (4.17 g, 19.6 mmol) were mixed with $Pd(OAc)_2$ (15 mg) and di-tert-butyl(2'-methyl-[1,1'-biphenyl]-2-yl)phosphine (39 mg), and diluted with toluene (25 ml). The resultant mixture was simply degassed via vacuum and charged with argon. Then it was heated at 90° C. for 24 h and at 110° C. for 5 hours. After aqueous work-up with EtOAc, the desired product-methyl 4-(2-ethoxy-2-oxoethyl)-3-methylbenzoate was isolated by column chromatography, eluting with EtOAc/Hexane (1/3), as oil (366 mg, 25%).

Step 2: Synthesis of 2-(4-(methoxycarbonyl)-2-methylphenyl)acetic acid: Methyl 4-(2-ethoxy-2-oxoethyl)-3-methylbenzoate (366 mg) was suspended in MeOH(10 ml) and $H_2O$ (2 ml) and treated with LiOH (48 mg) over 3 days. After the reaction mixture was acidified with 1N HCl, the product was extracted with EtOAc. Evaporation and drying in vacuum afforded the desired product (295 mg).

Step 3: Synthesis of Intermediate J: 2-(4-(methoxycarbonyl)-2-methylphenyl)acetic acid (295 mg) was treated with resorcinol (190 mg) in $BF_3Et_2O$ at 90° C. over night. After aqueous work-up with ethyl acetate and column purification, the desired product (296 mg) was isolated as an oil.

Intermediate K 4-(2-(2,4-dihydroxyphenyl)-2-oxoethyl)benzonitrile

Synthesis: A mixture of 2-(4-bromophenyl)-1-(2,4-dihydroxyphenyl)ethanone (Step 1, Intermediate D) (5 g, 16.3 mmol) and CuCN (5.8 g, 65.4 mmol) in DMF (50 ml) was stirred at 150° C. for 6 h under the protection of nitrogen. Water (100 ml) and EtOAc (100 ml) was added to the mixture. The precipitate was filtered off and the filtrate was washed with brine (100 ml), dried over $Na_2SO_4$ and concentrated to give black oil, which was purified by Combiflash (PE/EtOAc=3/1) to afford Intermediate K as a yellow powder (1.5 g, 36.6%).

Intermediate L methyl 4-(2-(3-fluoro-2,4-dihydroxyphenyl)-2-oxoethyl)benzoate

Intermediate L can be prepared following the procedure described for Intermediate K, Step 3, starting from 2-(4-(methoxycarbonyl)phenyl)acetic acid (synthesis is described in PCT/US2010/024035) and 2-fluorobenzene-1,3-diol (commercially available).

Example 26

GSNOR Assays

Various compounds were tested in vitro for their ability to inhibit GSNOR activity. GSNOR inhibitor compounds in Examples 1-22 had an $IC_{50}$ of about <1 μM. GSNOR inhibitor compounds in Examples 1-3, 5-6, 8-9, 11-12, 14, 16-22 had an $IC_{50}$ of about less than 0.1 μM.

GSNOR expression and purification is described in Biochemistry 2000, 39, 10720-10729.

GSNOR fermentation: Pre-cultures were grown from stabs of a GSNOR glycerol stock in 2XYT media containing 100 μg/ml ampicillin after an overnight incubation at 37° C. Cells were then added to fresh 2XYT (4 L) containing ampicillin and grown to an OD ($A_{600}$) of 0.6-0.9 at 37° C. before induction. GSNOR expression was induced with 0.1% arabinose in an overnight incubation at 20° C.

GSNOR Purification: E. coli cell paste was lysed by nitrogen cavitation and the clarified lysate purified by Ni affinity chromatography on an AKTA FPLC (Amersham Pharmacia). The column was eluted in 20 mM Tris pH 8.0/250 mM NaCl with a 0-500 mM imidazole gradient. Eluted GSNOR fractions containing the Smt-GSNOR fusion were digested overnight with Ulp-1 at 4° C. to remove the affinity tag then re-run on the Ni column under the same conditions. GSNOR was recovered in the flowthrough fraction and for crystallography is further purified by Q-Sepharose and Heparin flowthrough chromatography in 20 mM Tris pH 8.0, 1 mM DTT, 10 uM $ZnSO_4$.

GSNOR Assay: GSNO and enzyme/NADH Solutions are made up fresh each day. The solutions are filtered and allowed to warm to room temperature. GSNO solution: 100 mM NaPO4 (pH 7.4), 0.480 mM GSNO. 396 μL of GSNO Solution is added to a cuvette followed by 8 μL of test compound in DMSO (or DMSO only for full reaction control) and mixed with the pipette tip. Compounds to be tested are made up at a stock concentration of 10 mM in 100% DMSO. 2 fold serial dilutions are done in 100% DMSO. 8 μL of each dilution are added to an assay so that the final concentration of DMSO in the assay is 1%. The concentrations of compounds tested range from 100 to 0.003 μM. Enzyme/NADH solution: 100 mM $NaPO_4$ (pH 7.4), 0.600 mM NADH, 1.0 μg/ml GSNO Reductase. 396 μL of the Enzyme/NADH solution is added to the cuvette to start the reaction. The cuvette is placed in the Cary 3E UV/Visible Spectrophotometer and the change in 340 nm absorbance/min at 25° C. is recorded for 3 minutes. The assays are done in triplicate for each compound concentration. $IC_{50}$'s for each compound are calculated using the standard curve analysis in the Enzyme Kinetics Module of SigmaPlot.

Final assay conditions: 100 mM $NaPO_4$, pH 7.4, 0.240 mM GSNO, 0.300 mM NADH, 0.5 μg/ml GSNO Reductase, and 1% DMSO. Final volume: 800 μL/cuvette.

Example 27

Efficacy of GSNOR1 in Experimental Asthma

Experimental Asthma Model:
A mouse model of ovalbumin (OVA)-induced asthma was used to screen GSNOR inhibitors for efficacy against methacholine (MCh)-induced bronchoconstriction/airway hyperresponsiveness. This is a widely used and well characterized model that presents with an acute, allergic asthma phenotype with similarities to human asthma. Efficacy of GSNOR inhibitors was assessed using a protocol in which GSNOR inhibitors were administered after OVA sensitization and airway challenge, and prior to challenge with MCh. Bronchoconstriction in response to challenge with increasing doses of MCh was assessed using whole body plethysmography ($P_{enh}$; Buxco). The amount of eosinophil infiltrate into the bronchoaveolar lavage fluid (BALF) was also determined as a measure of lung inflammation. The effects of GSNOR inhibitors were compared to vehicles and to Combivent (inhaled; 1H) as the positive control.

Materials and Method

Allergen Sensitization and Challenge Protocol

OVA (500 µg/ml) in PBS was mixed with equal volumes of 10% (w/v) aluminum potassium sulfate in distilled water and incubated for 60 min. at room temperature after adjustment to pH 6.5 using 10 N NaOH. After centrifugation at 750×g for 5 min, the OVA/alum pellet was resuspended to the original volume in distilled water. Mice received an intraperitoneal (IP) injection of 100 µg OVA (0.2 ml of 500 µg/ml in normal saline) complexed with alum on day 0. Mice were anesthetized by IP injection of a 0.2-ml mixture of ketamine and xylazine (0.44 and 6.3 mg/ml, respectively) in normal saline and were placed on a board in the supine position. Two hundred fifty micrograms (100 µl of a 2.5 mg/ml) of OVA (on day 8) and 125 µg (50 µl of 2.5 mg/ml) OVA (on days 15, 18, and 21) were placed on the back of the tongue of each animal.

Pulmonary Function Testing (Penh)

In vivo airway responsiveness to methacholine was measured 24 h after the last OVA challenge in conscious, freely moving, spontaneously breathing mice with whole body plethysmography using a Buxco chamber (Wilmington, N.C.). Mice were challenged with aerosolized saline or increasing doses of methacholine (5, 20, and 50 mg/ml) generated by an ultrasonic nebulizer for 2 min. The degree of bronchoconstriction was expressed as enhanced pause ($P_{enh}$), a calculated dimensionless value, which correlates with the measurement of airway resistance, impedance, and intrapleural pressure in the same mouse. $P_{enh}$ readings were taken and averaged for 4 min. after each nebulization challenge. $P_{enh}$ is calculated as follows: $P_{enh}=[(T_e/T_r-1)\times(PEF/PIF)]$, where $T_e$ is expiration time, $T_r$ is relaxation time, PEF is peak expiratory flow, and PIF is peak inspiratory flow×0.67 coefficient. The time for the box pressure to change from a maximum to a user-defined percentage of the maximum represents the relaxation time. The $T_r$ measurement begins at the maximum box pressure and ends at 40%.

Eosinophil Infiltrate in BALF

After measurement of airway hyper-reactivity, the mice were exsanguinated by cardiac puncture, and then BALF was collected from either both lungs or from the right lung after tying off the left lung at the mainstem bronchus. Total BALF cells were counted from a 0.05 ml aliquot, and the remaining fluid was centrifuged at 200×g for 10 min at 4° C. Cell pellets were resuspended in saline containing 10% BSA with smears made on glass slides. Eosinophils were stained for 5 min. with 0.05% aqueous eosin and 5% acetone in distilled water, rinsed with distilled water, and counterstained with 0.07% methylene blue. Alternatively, eosinophils and other leukocytes were stained with DiffQuik.

GSNOR Inhibitors and Controls

GSNOR inhibitors were reconstituted in phosphate buffered saline (PBS), pH 7.4, or 0.5% w/v carboxy methylcellulose at concentrations ranging from 0.00005 to 3 mg/ml. GSNOR inhibitors were administered to mice (10 ml/kg) as a single dose or multiple dose either intravenously (IV) or orally via gavage. Dosing was performed from 30 min. to 72 h prior to MCh challenge. Effects of GSNOR inhibitors were compared to vehicle dosed in the same manner.

Combivent was used as the positive control in all studies. Combivent (Boehringer Ingelheim) was administered to the lung using the inhaler device supplied with the product, but adapted for administration to mice, using a pipet tip. Combivent was administered 48 hours, 24 hours, and 1 h prior to MCh challenge. Each puff (or dose) of Combivent provides a dose of 18 µg ipatropium bromide (IpBr) and 103 µg albuterol sulfate or approximately 0.9 mg/kg IpBr and 5 mg/kg albuterol.

Statistical Analyses

Area under the curve values for $P_{enh}$ across baseline, saline, and increasing doses of MCh challenge were calculated using GraphPad Prism 5.0 (San Diego, Calif.) and expressed as a percent of the respective (IV or orally administered) vehicle control. Statistical differences among treatment groups and the respective vehicle control group within each study were calculated using one-way ANOVA, Dunnetts or Bonferroni post-hoc tests or t-test (JMP 8.0, SAS Institute, Cary, N.C. or Microsoft Excel). A p value of <0.05 among the treatment groups and the respective vehicle control group was considered significantly different.

Results

In the OVA model of asthma, the compound of Example 3 decreased the AUC for Penh (p<0.05) and eosinophil infiltration into BALF by 43% and 42%, respectively, of vehicle control when given via a single oral dose of 10 mg/kg at 24 h prior to assessment. In another study, the compound of Example 3 decreased eosinophil infiltration in BALF by 12% of vehicle control when given via three oral doses of 10 mg/kg at 48 hours, 24 hours, and 1 h prior to assessment.

In the OVA model of asthma, the compound of Example 1 decreased the AUC for Penh (p<0.05) and eosinophil infiltration into BALF by 20% to 39% and 0% to 31%, respectively, of vehicle control when given via a single oral dose of 10 mg/kg at 24 h prior to assessment. The compound of Example 1 significantly decreased the AUC for Penh by 39% of vehicle control when given via a single IV dose of 10 mg/kg at 24 h prior to assessment.

In the OVA model of asthma, the compound of Example 9 significantly decreased the AUC for Penh and eosinophil infiltration into BALF by 18% and 82%, respectively, of vehicle control when given via a single oral dose of 10 mg/kg at 24 h prior to assessment.

In the OVA model of asthma, the compound of Example 16 significantly (p<0.05) decreased eosinophil infiltration in BAL by 36% of vehicle control when given via three oral doses of 10 mg/kg at 48 hours, 24 hours, and 1 h prior to assessment.

Example 28

Mouse Pharmacokinetic (PK) Study

Experimental Model

The mouse was used to determine the pharmacokinetics of compounds of the invention. This species is widely used to assess the bioavailability of compounds by administering both oral (PO) and intravenous (IV) test articles. Efficacy of the compounds of the invention was compared by assessing plasma exposure in male BALB/c mice either via IV or PO administration at the times of peak activity.

Materials and Methods

IV Administration of Compounds of the Invention

Compounds of the invention were reconstituted in a phosphate buffered saline (PBS)/10% Solutol (HS 15) clear solution resulting in a concentration of 0.2 mg/ml and administered to mice (2 mg/kg) as a single IV dose. Animals were dosed via the lateral tail vein. Blood samples were collected at designated time points (0.083, 0.25, 0.5, 1, 2, 4, 8, 16, 24 hours) by cardiac puncture under isoflurane anesthesia (up to 1 ml blood per animal). The blood was collected into tubes containing Li-Heparin. The blood samples were kept on ice until centrifugation within approximately 30 minutes of collection. The plasma was transferred into labeled polypropylene tubes and frozen at −70° C. until analyzed by LC/MS/MS.

PO Administration of Compounds of the Invention

The compounds of the invention were reconstituted in 40% Propylene Glycol/40% Propylene Carbonate/20% of a 5% Sucrose clear solution resulting in a concentration of 2 mg/ml and administered to mice (10 mg/kg) as a single oral dose via gavage. Blood samples were collected at 0.25, 0.5, 1, 2, 4, 8, 12, 16, 20 and 24 hours post dose by cardiac puncture under isoflurane anesthesia. The blood was collected in tubes containing Li-Heparin. The blood samples were kept on ice until centrifugation within approximately 30 minutes of collection. The plasma was transferred into labeled polypropylene tubes and frozen at −70° C. until analyzed by LC/MS/MS.

LC/MS/MS Analysis

Plasma samples at each time point were analyzed using a LC-MS/MS with a lower limit of quantification (LLOQ) of 1 ng/ml. Plasma was analyzed to determine the amount of the compound of the invention in each sample and regression curves generated for each compounds of the invention in the relevant matrixes.

WinNonlin analysis was used for calculating PK parameters for both the IV and PO administrations:

PK parameters for IV portion—$AUC_{last}$; $AUC_{INF}$; T1/2; Cl; Vss; $C_{max}$; MRT PK parameters for PO portion—$AUC_{last}$; $AUC_{INF}$; T1/2; $C_{max}$; Cl, MRT.

In addition to the above PK parameters, bioavailability (% F) was calculated.

Results:

The compounds of Examples 1, 3, 9 and 12 had an oral bioavailability of about 4-41%. The compound of example 16 had an oral bioavailability of about 44%. A comparator compound 4-(7-hydroxy-4-oxo-2-(trifluoromethyl)-4H-chromen-3-yl)benzoic acid (see PCT/US2010/024035) had an oral bioavailability of about 17%. The comparator compound is cleared (Cl) about three times faster than Example 16.

Example 29

Efficacy of GSNOR Inhibitors in Experimental Inflammatory Bowel Disease (IBD)

Overview of the Models:

Acute and chronic models of dextran sodium sulfate (DSS)-induced IBD in mice were used to explore efficacy of GSNORi against this disease. Acute and chronic DSS-induced IBD are widely used and well characterized models that induce pathological changes in the colon similar to those observed in the human disease. In these models and in human disease, epithelial cells within the crypts of the colon are disrupted, leading to dysfunction of the epithelial barrier and the ensuing tissue inflammation, edema, and ulceration. GSNORi therapy may benefit IBD by restoring s-nitrosoglutathione (GSNO) levels, and thus prevent or reverse the epithelial barrier dysfunction.

Acute Prophylactic Model:

Experimental IBD was induced by administration of DSS in the drinking water of male C57B1/6 mice (N=8 to 10 mice per group) for 6 consecutive days. GSNORi was dosed orally at doses of 0.1 to 10 mg/kg/day for 10 days starting two days prior to and continuing two days post DSS exposure. Two days post DSS exposure, the effect of GSNORi was assessed in a blinded fashion via endoscopy and histopathology using a five point scale ranging from a score=0 (normal tissue) through a score=4 (ulcerative tissue damage and marked pathological changes). Levels of circulating cytokines involved in inflammatory pathways were also assessed. The effect of GSNORi was compared to vehicle treated controls. The corticosteroid, prednisolone, was used as the positive control in this study and was administered daily at 3 mg/kg/day via oral dosing. Naïve mice (N=5) were also assessed as a normal tissue control.

Chronic Treatment Model:

Experimental IBD was induced by administration of DSS in the drinking water of male C57B1/6 mice (N=10 to 12 mice per group) for 6 consecutive days. GSNORi was dosed orally at doses of 10 mg/kg/day for 14 days starting one day after cessation of DSS exposure. Efficacy of GSNORi was assessed in a blinded fashion via endoscopy after 7 days and 14 days of GSNORi dosing and via histopathology after 14 days of GSNORi dosing using a five point scale ranging from a score=0 (normal tissue) through a score=4 (ulcerative tissue damage and marked pathological changes). Levels of circulating cytokines involved in inflammatory pathways were also assessed. The effect of GSNORi was compared to vehicle treated controls. The corticosteroid, prednisolone, was used as the positive control in this study and was administered daily at 3 mg/kg/day via oral dosing. Naïve mice (N=5) were also assessed as a normal tissue control.

Results:

The compound of Example 3 attenuated colon injury in a mouse model of acute DSS-induced IBD. The percent of mice presenting with severe colon injury scores via endoscopy assessment was decreased by 38% or 25% of vehicle control after oral treatment with 0.1 or 1 mg/kg/day, respectively, of the compound of Example 3 for 10 consecutive days using a prophylactic dosing regimen. The percent of mice presenting with severe colon injury scores via pathology assessment was decreased by 12% or 33% of vehicle control after oral treatment with 0.1 or 1 mg/kg/day, respectively, of the compound of Example 3 for 10 days.

The compound of Example 1 attenuated colon injury in a mouse model of acute DSS-induced IBD. The percent of mice presenting with severe colon injury scores via endoscopy or histopathology assessment was decreased by 75% or 17%, respectively, of vehicle control after oral treatment with 10 mg/kg/day of the compound of Example 1 for 10 consecutive days using a prophylactic dosing regimen.

The compound of Example 16 attenuated colon injury in a mouse model of acute DSS-induced IBD. The percent of mice presenting with severe colon injury scores via endoscopy or histopathology assessments was decreased by 58% or 15%, respectively, of vehicle control after oral treatment with the compound of Example 16 at 10 mg/kg/day for 10 consecutive days using a prophylactic dosing regimen.

Example 30

Efficacy of GSNOR Inhibitors in Experimental Chronic Obstructive Pulmonary Disease (COPD)

Short Duration Cigarette Smoke COPD Models

The efficacy of GSNOR inhibitors was assessed in a mouse model of chronic obstructive pulmonary disease (COPD) induced by short duration (4 days or 11 days) of exposure to cigarette smoke. Infiltration of inflammatory cells into the bronchoalveolar lavage fluid (BALF) and BALF levels of chemokines involved in inflammation and tissue turnover/repair were measured to assess the influences of GSNOR inhibitors on some of the early events associated with the initiation and progression of COPD.

Overview of the Models:

Efficacy of GSNOR inhibitors against COPD was explored using acute (4 day) and subchronic (11 day) models of cigarette smoke-induced COPD in mice. Exposure of animals to cigarette smoke provides a model of COPD in which injury is induced by the same causative agent as in human disease and in which injury exhibits similarities to the human disease, including airway obstruction, airspace enlargement, and involvement of inflammatory responses in these pathologies. In animal models, changes in lung pathology are only evident after extended (several months) duration of exposure to cigarette smoke, thus making chronic models prohibitive as effective screening tools. More recently, models exploring inflammatory responses after short duration (2 weeks or less) of smoke exposure in mice have been utilized as tools for screening efficacy and mechanisms of action of novel therapeutics against COPD. The key roles of inflammation in the initiation and progression of COPD, make these short duration models relevant for initial tests of efficacy of novel therapeutics.

Acute (4 Day) Smoke Exposure Model:

Female C57B1/6 mice (N=8 per group) were exposed to cigarette smoke using a whole body exposure chamber. Mice were exposed daily for 4 consecutive days to 4 cycles of smoke from 6 sequential cigarettes (Kentucky 3R4F without filter) with a 30 minute smoke free interval between cycles. GSNOR inhibitors were administered daily via oral dosing at 10 mg/kg/day for 7 days starting 2 days prior to smoke exposure and continuing 1 day post-exposure. The effects of GSNOR inhibitors were assessed by quantitating the numbers of total cells, leukocytes, and leukocytes differentials in the BALF via light microscopy and the levels of BALF chemokines via ELISA at approximately 24 h after the last smoke exposure. The effect of GSNOR inhibitors were compared to vehicle treated controls. The PDE4 inhibitor, roflumilast, was used as the positive control for the study. A group of naïve mice (N=8) was exposed to air and used as a negative control for the study.

Subchronic (11 Day) Smoke Exposure Model:

Female C57B1/6 mice (N=10 per group) were exposed to cigarette smoke generated from Marlboro 100 cigarettes without filters. Exposure times were 25 min. on study day 1, 35 min. on study day 2, and 45 min. on study days 3 to 11. GSNOR inhibitors were administered one hour prior to smoke exposure on each day. GSNOR inhibitors were dosed orally at 1 to 10 mg/kg/day for 11 days. The effects of GSNOR inhibitors were assessed by quantitating the number of total cells, and leukocytes differentials in the BALF via light microscopy at 24 h after the last exposure. The effect of GSNOR inhibitors were compared to vehicle treated controls and expressed as percent inhibition of the cigarette smoke induced increases in BALF cell numbers. Roflumilast was used as the positive control for the study and was dosed at 5 mg/kg/day. A group of naïve mice (N=10) was exposed to air and dosed with vehicle as a negative control for the study.

Results:

The compound of Example 3 attenuated the smoke-induced changes in BALF cellular infiltrate and BALF inflammatory chemokines. Example 3 completely (100%) and significantly ($p<0.05$) inhibited the smoke-induced increase in total cells, leukocytes, macrophages, neutrophils, and eosinophils in BALF compared to vehicle treated controls when dosed orally at 10 mg/kg/day for 7 days in the acute 4 day smoke model. These effects of Example 3 were comparable to or greater than those observed for roflumilast. Example 3 also restored BALF chemokines towards levels observed in naïve mice. In the subchronic 11 day model, the compound of Example 3 inhibited the smoke-induced increase in total cells ($p<0.05$), macrophages ($p<0.05$), neutrophils, eosinophils, and lymphocytes in BALF by 26%, 28%, 25%, 57%, and 24%, respectively, when dosed orally at 10 mg/kg/day for 11 days.

The compound of Example 16 significantly ($p<0.05$) inhibited the smoke-induced increase in total cells, macrophages, neutrophils, and lymphocytes in BAL by 53%, 44%, 68%, and 62%, respectively, when dosed orally at 1 mg/kg/day for 11 days in the subchronic 11 day model. The effects of Example 16 were comparable to those of roflumilast.

* * *

It will be apparent to those skilled in the art that various modifications and variations can be made in the methods and compositions of the present invention without departing from the spirit or scope of the invention.

What is claimed is:

1. A compound or a pharmaceutically acceptable salt thereof selected from the group consisting of 3-fluoro-4-(7-hydroxy-4-oxo-2-(trifluoromethyl)-4H-chromen-3-yl)benzoic acid, 4-(7-hydroxy-4-oxo-2-(trifluoromethyl)-4H-chromen-3-yl)-3-methylbenzoic acid and 4-(8-flouoro-7-hydroxy-4-oxo-2-(trifluoromethyl)-4H-chromen-3-yl)-3-methylbenzoic acid.

2. A pharmaceutical composition comprising a therapeutically effective amount of a compound according to claim 1 together with a pharmaceutically accepted carrier or excipient.

* * * * *